(12) United States Patent
Shibata et al.

(10) Patent No.: US 7,940,887 B2
(45) Date of Patent: May 10, 2011

(54) RADIOGRAPHIC APPARATUS

(75) Inventors: Koichi Shibata, Kyoto (JP); Kazuhiro Mori, Kyoto (JP); Shingo Baba, Kyoto (JP); Daisuke Notohara, Kyoto (JP); Shinya Hirasawa, Kyoto (JP); Keiichi Goto, Kyoto (JP); Yukio Mishina, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 64 days.

(21) Appl. No.: 12/376,765

(22) PCT Filed: Aug. 8, 2007

(86) PCT No.: PCT/JP2007/065545
§ 371 (c)(1),
(2), (4) Date: Feb. 6, 2009

(87) PCT Pub. No.: WO2008/018510
PCT Pub. Date: Feb. 14, 2008

(65) Prior Publication Data
US 2010/0189214 A1    Jul. 29, 2010

(30) Foreign Application Priority Data

Aug. 8, 2006  (JP) ................................. 2006-215982

(51) Int. Cl.
*A61B 6/00* (2006.01)
(52) U.S. Cl. ................................. 378/21; 378/5; 378/8
(58) Field of Classification Search ............... 378/4, 8, 378/21
See application file for complete search history.

(56) References Cited

U.S. PATENT DOCUMENTS

| 4,477,922 | A  | * | 10/1984 | Liebetruth | ..................... 378/20 |
| 4,570,263 | A  | * | 2/1986  | Liebetruth | ..................... 378/20 |
| 2002/0154728 | A1 | * | 10/2002 | Morita et al. | ..................... 378/4 |
| 2004/0066882 | A1 | * | 4/2004  | Eberhard et al. | .............. 378/19 |
| 2004/0247081 | A1 |   | 12/2004 | Halsmer et al. | |
| 2005/0053191 | A1 |   | 3/2005  | Gohno et al. | |
| 2005/0078785 | A1 | * | 4/2005  | Endo | ............................. 378/22 |

(Continued)

FOREIGN PATENT DOCUMENTS

JP    2000-350717 A    12/2000

(Continued)

OTHER PUBLICATIONS

Korean Office Action for the Application No. 10-2008-7032023 from Korean Patent Office dated Jun. 11, 2010.

(Continued)

*Primary Examiner* — Edward J Glick
*Assistant Examiner* — Alexander H Taningco
(74) *Attorney, Agent, or Firm* — Cheng Law Group, PLLC

(57) ABSTRACT

An X-ray tube and a flat panel X-ray detector (FPD) are constructed movable parallel to each other in the same direction along a body axis which is a longitudinal direction of a patient. The X-ray tube intermittently emits radiation and the FPD detects radiation transmitted through the patient irradiated intermittently whenever the X-ray tube and FPD move every pitch. X-ray images $O_1, O_2, \ldots, O_I, \ldots,$ and $O_M$ are decomposed for every pitch noted above. The decomposed images are composed for each projection angle to obtain projection images $P_1, P_2$ and so on. Therefore, a sectional image with a long field of view in the longitudinal direction can be obtained by carrying out a reconstruction process based on the composed projection images.

4 Claims, 17 Drawing Sheets

U.S. PATENT DOCUMENTS

| | | |
|---|---|---|
| 2005/0094760 A1 | 5/2005 | Hagiwara |
| 2005/0185755 A1* | 8/2005 | Okamura .................. 378/22 |

FOREIGN PATENT DOCUMENTS

| | | |
|---|---|---|
| JP | 2001-269333 A | 10/2001 |
| JP | 2002-537050 A | 11/2002 |
| JP | 2003-052680 A | 2/2003 |
| JP | 2004-113408 A | 4/2004 |
| JP | 2004-236929 A | 8/2004 |
| JP | 2004-358255 A | 12/2004 |
| JP | 2005-046444 A | 2/2005 |
| JP | 2005-270277 A | 10/2005 |
| JP | 2005-296332 A | 10/2005 |
| JP | 2006-071472 A | 3/2006 |
| KR | 10-2005-0025914 A | 3/2005 |
| KR | 10-2005-0042727 A | 5/2005 |
| WO | WO-00/49572 A1 | 8/2000 |

OTHER PUBLICATIONS

International Search Report for the Application No. PCT/JP2007/065545 mailed Nov. 13, 2007.

* cited by examiner

Fig.9
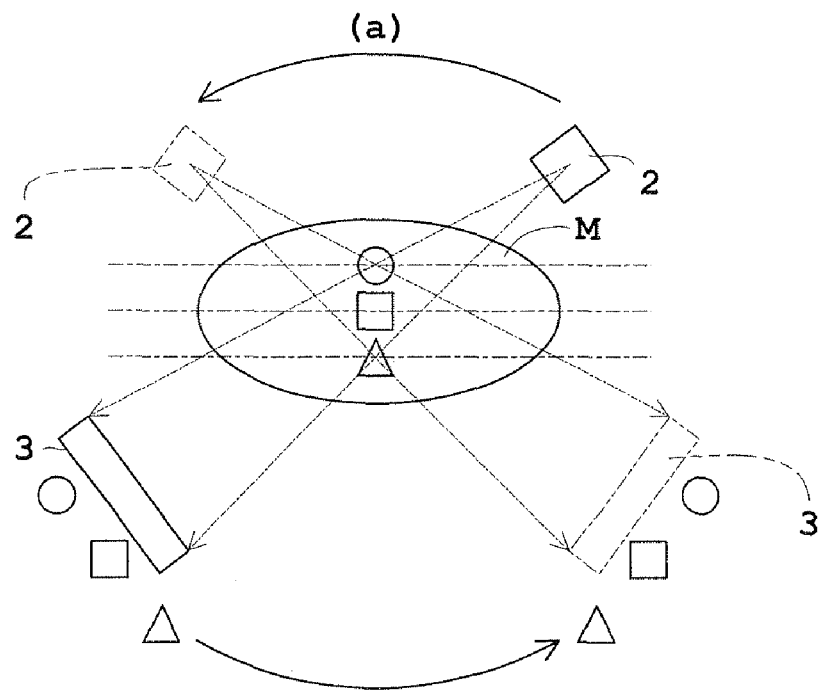
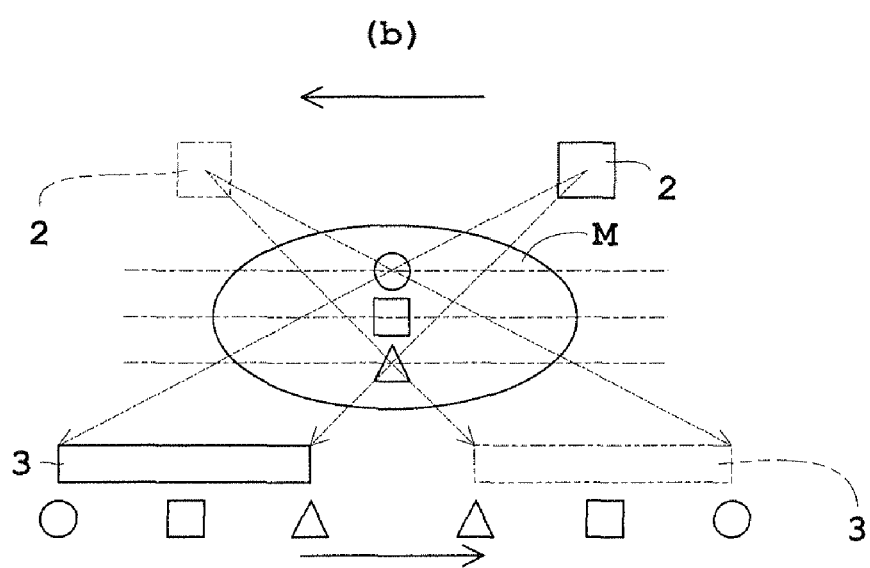

$\beta = \Phi$

Fig.13
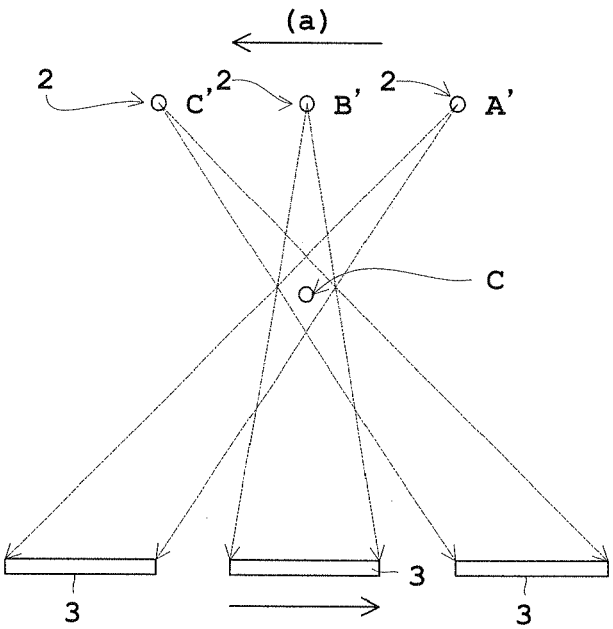
(a)
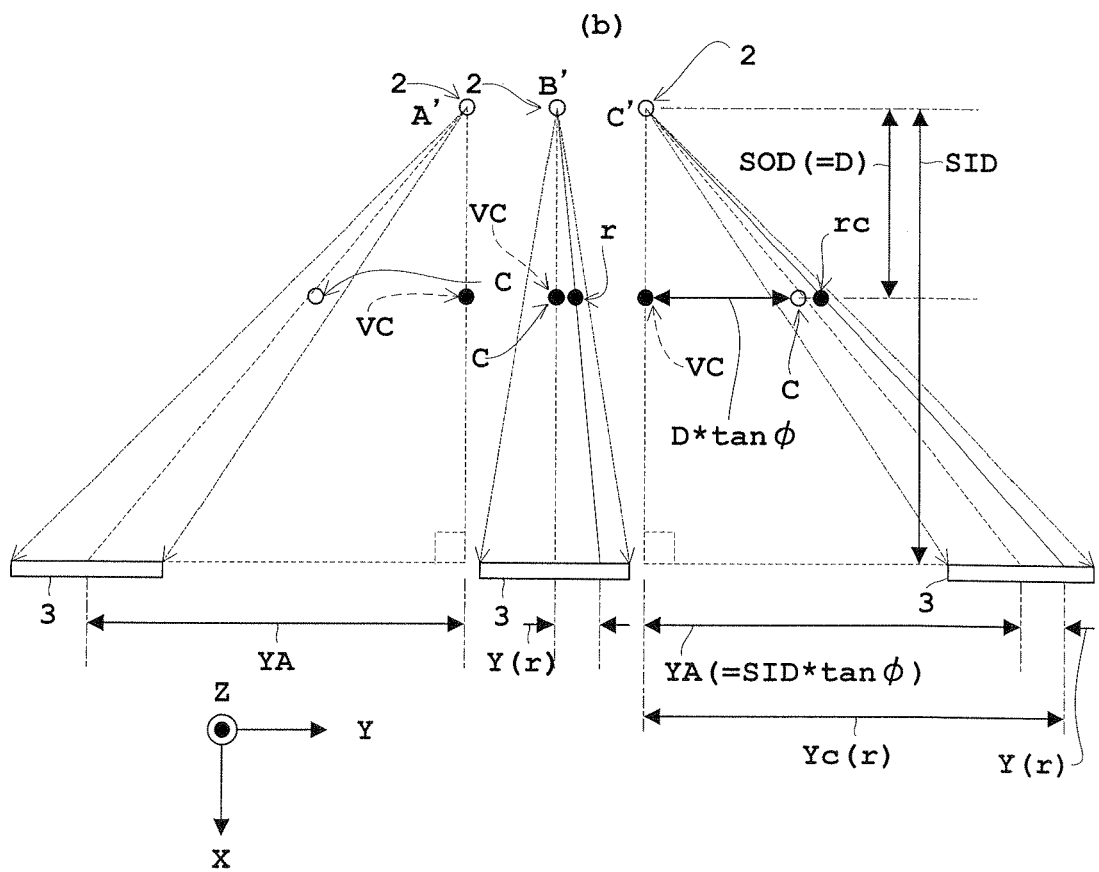
(b)

RADIOGRAPHIC APPARATUS

TECHNICAL FIELD

This invention relates to a radiographic apparatus for carrying out a radiation image pickup by obtaining radiographic images based on radiation detected, and more particularly to a technique for obtaining sectional images through a reconstruction process.

BACKGROUND ART

Radiographic apparatus which obtain sectional images through a reconstruction process include an X-ray CT (computed tomography) apparatus and an X-ray body section imaging apparatus. In the X-ray CT apparatus, sectional images are obtained by an X-ray tube (radiation emitting device) and an X-ray detector (radiation detecting device) rotating about the body axis extending longitudinally of a patient. In the X-ray body section imaging apparatus, as shown in FIG. 20, for example, sectional images are obtained by an X-ray tube 101 and an X-ray detector 102 making parallel translation in opposite directions along the body axis z of a patient M. In the case of the X-ray body section imaging apparatus, compared with the X-ray CT apparatus, the resolution of sectional images obtained is inferior, but there is an advantage that sectional images can be obtained through parallel translation. The image pickup mode adopted in such X-ray CT apparatus and X-ray body section imaging apparatus is an image pickup method effective for many sites such as the chest, joints and digestive organs.

On the other hand, there has been an X-ray apparatus in recent years which obtains X-ray images along the body axis of a patient by moving an X-ray tube and an X-ray detector in parallel to each other in the same direction along the body axis of the patient (see Patent Document 1, for example). The X-ray images obtained with this apparatus are projection data of projected X rays (projection images). Since the X-ray tube and X-ray detector move parallel to each other in the same direction along the body axis, the projection angle can be maintained at substantially the same angle. Therefore, X-ray images can be obtained of a long area (long X-ray images) in the longitudinal direction which is the direction of the body axis.

[Patent Document 1]

Unexamined Patent Publication No. 2004-236929 (pages 1-8, FIGS. 1, 6 and 10)

DISCLOSURE OF THE INVENTION

Problem to be Solved by the Invention

However, the above X-ray body section imaging apparatus has a limited field of view. An image intensifier (I. I) or the like was used as the X-ray detector in the past, but in recent years a flat panel X-ray detector (hereinafter abbreviated as "FPD") has been used as shown in FIG. 20. The FPD, with the detecting plane being a flat plane, has a larger field of view than the image intensifier. However, with the X-ray body section imaging apparatus, the farther from the area of interest, the lower becomes the resolution noted above. Since the X-ray tube 101 and X-ray detector 102 move parallel to each other in opposite directions, resolution will fall as the angle formed between the radiation axis connecting the X-ray detector 102 and X-ray tube 101 and the body axis z of the patient (hereinafter called the "projection angle") deviates from the vertical to become an acute angle or obtuse angle. As a result, the field of view is limited even when the FPD is used as the X-ray detector. Thus, tomography with a field of view long in the direction of the body axis is desired.

This invention has been made having regard to the state of the art noted above, and its object is to provide a radiographic apparatus which can obtain sectional images with a long field of view.

Means for Solving the Problem

To solve the above problem, Inventor has made intensive research and attained the following findings.

That is, attention has been directed to the X-ray apparatus which obtains a long X-ray image in the longitudinal direction as in Patent Document 1 noted above. Then, a long X-ray image can be obtained in the longitudinal direction if a construction is made as in this X-ray apparatus in which a radiation emitting device represented by the X-ray tube and a radiation detecting device represented by the X-ray detector move parallel to each other in the same direction along a longitudinal direction which is the direction of the body axis of a patient. On the other hand, since the long X-ray image obtained in Patent Document 1 is a projection image, a further image pickup mode and a construction for obtaining sectional images are needed.

Then, as the former, further image pickup mode, radiation is intermittently emitted from the radiation emitting device whenever the radiation emitting device and radiation detecting device move every predetermined distance, and the radiation detecting device detects radiation transmitted through the patient irradiated intermittently. As the latter construction for obtaining sectional images, radiographic images are decomposed for every predetermined distance noted above, and the decomposed images are composed for every projection angle to obtain a projection image for every projection angle. It has been found that a sectional image with a long field of view in the longitudinal direction can be obtained through a reconstruction process based on the composed projection images.

Based on the above findings, this invention provides the following construction.

A radiographic apparatus according to this invention is a radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device and the radiation detecting device being constructed movable parallel relative to each other in the same direction along a longitudinal direction of the patient, the radiation emitting device intermittently emitting radiation and the radiation detecting device detecting radiation transmitted through the patient irradiated intermittently whenever the radiation emitting device and the radiation detecting device move every predetermined distance relative to the patient, said apparatus comprising an image decomposing device for decomposing the radiographic image for the every predetermined distance, an image composing device for composing the decomposed images for each of the same projection angles to obtain a projection image for each projection angle, and a reconstruction processing device for carrying out a reconstruction process based on the composed projection images to obtain a sectional image.

According to the radiographic apparatus of this invention, data with a long field of view in the longitudinal direction can be obtained from the radiation detecting device, by constructing the radiation emitting device and the radiation detecting device to be movable parallel relative to each other in the same direction along the longitudinal direction of the patient. On the other hand, the radiation emitting device intermittently emits radiation and the radiation detecting device detects radiation transmitted through the patient irradiated intermittently whenever the radiation emitting device and the radiation detecting device move every predetermined distance relative to the patient. And the image decomposing device decomposes the radiographic image for the every predetermined distance, and the image composing device composes the decomposed images for each of the same projection angles to obtain a projection image for each projection angle. Thus, the reconstruction processing device carries out a reconstruction process based on the composed projection images, thereby to obtain a sectional image with a long field of view in the longitudinal direction.

In the invention noted above, preferably, the radiation emitting device and the radiation detecting device are movable parallel relative to each other at an equal speed relative to the patient. With the radiation emitting device and the radiation detecting device movable parallel relative to each other at an equal speed relative to the patient, the projection angle can be maintained at the same angle, and the relative movement of the radiation emitting device and the radiation detecting device can be carried out longer. As a result, a sectional image with a longer field of view can be obtained.

In one example of these inventions noted above, an output device is provided for outputting the sectional image obtained by the reconstruction processing device. With the output device provided, it is possible to browse outputs. The output device may be a display device represented by a monitor for outputting displays, or a printing device represented by a printer for outputting prints.

EFFECTS OF THE INVENTION

With the radiographic apparatus according to this invention, the radiation emitting device and the radiation detecting device are constructed movable parallel relative to each other in the same direction along the longitudinal direction of the patient. The radiation emitting device is constructed to intermittently emit radiation and the radiation detecting device to detect radiation transmitted through the patient irradiated intermittently whenever the radiation emitting device and the radiation detecting device move every predetermined distance relative to the patient. The image decomposing device decomposes the radiographic image for the every predetermined distance, and the image composing device composes the decomposed images for each of the same projection angles to obtain a projection image for each projection angle. Thus, the reconstruction processing device carries out a reconstruction process based on the composed projection images, thereby to obtain a sectional image with a long field of view in the longitudinal direction.

BRIEF DESCRIPTION OF THE DRAWINGS

FIG. 9($a$) is a schematic view of arcuate track body section radiography, and ($b$) is a schematic view of linear track body section radiography;
FIG. 13($a$) and ($b$) are schematic views illustrating a method of applying Feldkamp to linear track body section radiography.

DESCRIPTION OF REFERENCES

2 . . . X-ray tube
3 . . . flat panel X-ray detector (FPD)
13 . . . monitor
9$b$ . . . image decomposing unit
9$c$ . . . image composing unit
9$d$ . . . reconstruction processing unit
d . . . pitch
z . . . body axis
M . . . patient Embodiment An embodiment of this invention will be described hereinafter with reference to the drawings.

Figure 1:
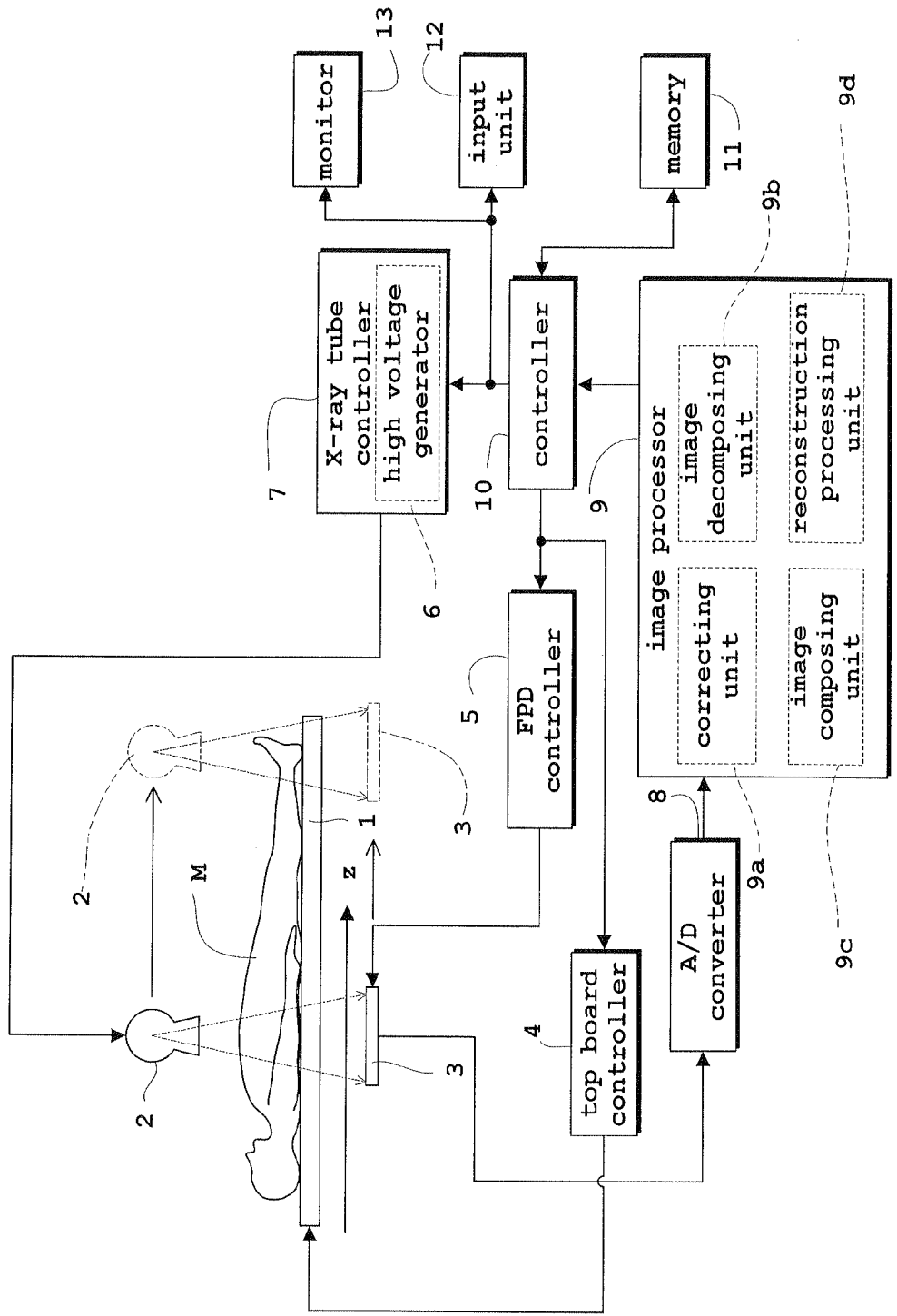
FIG. 1 is a block diagram of an X-ray body section imaging apparatus according to an embodiment.
Figure 2:
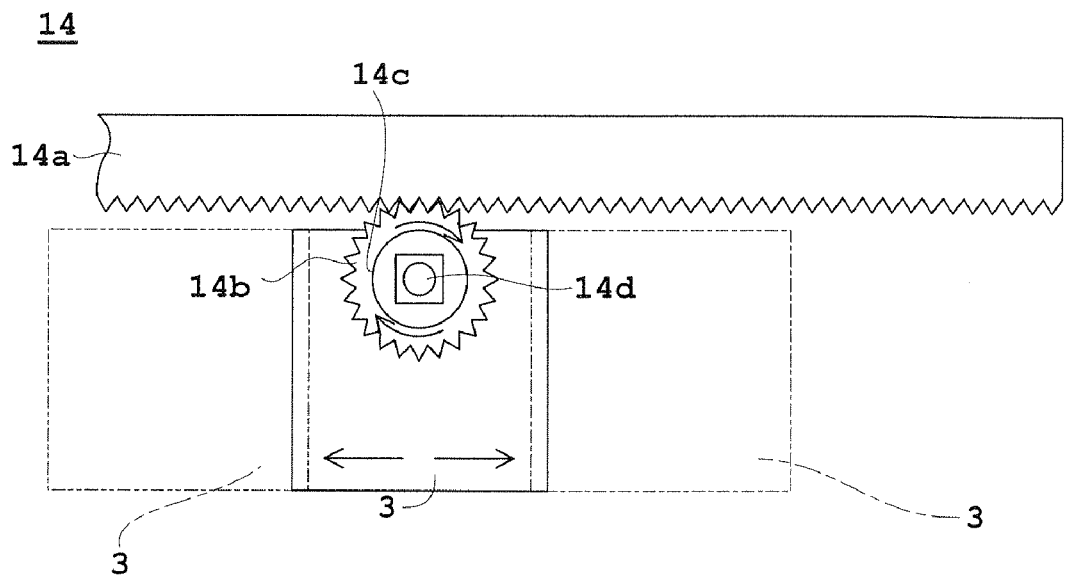
FIG. 2 is a schematic view showing an outline of an FPD drive mechanism relating to driving of a flat panel X-ray detector (FPD)
Figure 3:
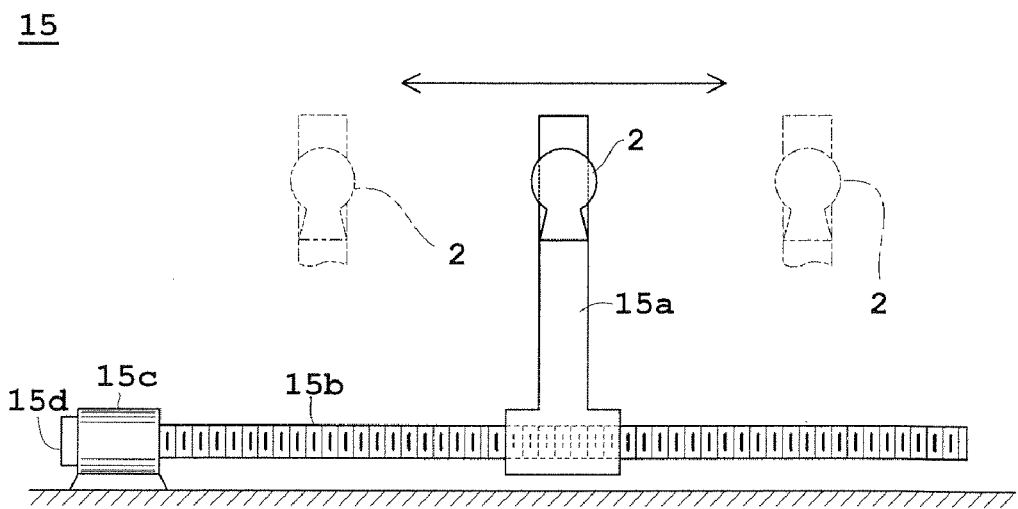
FIG. 3 is a schematic view showing an outline of an X-ray tube driver relating to driving of an X-ray tube.

FIG. 1 is a block diagram of an X-ray body section imaging apparatus according to the embodiment. FIG. 2 is a schematic view showing an outline of an FPD drive mechanism relating to driving of a flat panel X-ray detector. FIG. 3 is a schematic view showing an outline of an X-ray tube driver relating to driving of an X-ray tube. This embodiment will be described, taking the flat panel X-ray detector (hereinafter abbreviated as "FPD") as an example of radiation detecting device, and the X-ray body section imaging apparatus as an example of radiographic apparatus.

As shown in FIG. 1, the X-ray body section imaging apparatus includes a top board 1 for supporting a patient M, an X-ray tube 2 for emitting X rays toward the patient M, and an FPD 3 for detecting X rays transmitted through the patient M. The X-ray tube 2 corresponds to the radiation emitting device in this invention. The FPD 3 corresponds to the radiation detecting device in this invention.

The X-ray body section imaging apparatus further includes a top board controller 4 for controlling vertical and horizontal movements of the top board 1, an FPD controller 5 for controlling scanning action of the FPD 3, an X-ray tube controller 7 having a high voltage generator 6 for generating a tube voltage and tube current for the X-ray tube 2, an analog-to-digital converter 8 for digitizing and fetching X-ray detection signals which are charge signals from the FPD 3, an image processor 9 for performing various processes based on the X-ray detection signals outputted from the analog-to-digital converter 8, a controller 10 for performing an overall control of these components, a memory 11 for storing processed images, an input unit 12 for the operator to input various settings, and a monitor 13 for displaying the processed images and other information. The monitor 13 corresponds to the output device in this invention.

The top board controller 4 controls movement of the top board 1, such as moving the top board 1 horizontally to place the patient M in an imaging position, vertically moving and/or rotating the top board 1 to set the patient M to a desired position, horizontally moving the top board 1 during an imaging operation, and horizontally moving the top board 1 to withdraw the patient M from the imaging position after the imaging operation. These controls are carried out by controlling a top board driving mechanism (not shown) including motors and encoders (not shown).

The FPD controller 5 controls the FPD 3 to make parallel translation along the direction of a body axis z which is a longitudinal direction of the patient M. As shown in FIG. 2, this control is carried out by controlling an FPD drive mechanism 14 including a rack 14a, a pinion 14b, a motor 14c and an encoder 14d. Specifically, the rack 14a extends along the direction of body axis z of the patient M. The pinion 14b supports the FPD 3, is in part meshed with the rack 14a, and is rotatable by rotation of the motor 14c. For example, when the motor 14c is rotated forward, the FPD 3 will make parallel translation along the rack 14a toward the feet of the patient M as shown in the alternate long and short dash line in FIG. 2. When the motor 14c is reversed, the FPD 3 will make parallel translation along the rack 14a toward the head of the patient M as shown in the two-dot chain line in FIG. 2. The encoder 14d detects a direction of rotation and an amount of rotation of the motor 14c corresponding to a direction of movement and an amount of movement (moving distance) of the FPD 3. Results of detection by the encoder 14d are sent to the FPD controller 5.

The high voltage generator 6 generates the tube voltage and tube current for application to the X-ray tube 2 to emit X rays. The X-ray tube controller 7 controls the X-ray tube 2 to make parallel translation along the direction of body axis z of the patient M. As shown in FIG. 3, this control is carried out by controlling an X-ray tube driver 15 including a strut 15a, a threaded rod 15b, a motor 15c and an encoder 15d. Specifically, the strut 15a carries and supports the X-ray tube 2 on an upper end portion thereof, and is screwed to the threaded rod 15b at a lower end portion. The threaded rod 15b extends along the direction of body axis z of the patient M and is rotatable by rotation of the motor 15c. For example, when the motor 15c is rotated forward, the X-ray tube 2 will make parallel translation with the strut 15a toward the feet of the patient M as shown in the alternate long and short dash line in FIG. 3. When the motor 15c is reversed, the X-ray tube 2 will make parallel translation with the strut 15a toward the head of the patient M as shown in the two-dot chain line in FIG. 3. The encoder 15d detects a direction of rotation and an amount of rotation of the motor 15c corresponding to a direction of movement and an amount of movement (moving distance) of the X-ray tube 2. Results of detection by the encoder 15d are sent to the X-ray tube controller 7.

In order that the X-ray tube 2 and FPD 3 make parallel translation in the same direction along the direction of body axis z of the patient M as shown in FIG. 1, the FPD controller 5 and X-ray tube controller 7 carry out controls so that the direction of rotation of the motor 14c in FIG. 2 and the direction of rotation of the motor 15c in FIG. 3 may be the same. In this embodiment, it is preferred that the X-ray tube 2 and FPD 3 make parallel translation at an equal speed. That is, the FPD controller 5 controls the amount of rotation of the motor 14c and the X-ray tube controller 7 controls the amount of rotation of the motor 15c, so that the amount of movement of the X-ray tube 2 and the amount of movement of the FPD 3 may be the same.

The X-ray tube controller 7 controls also setting of an irradiation field of a collimator (not shown) adjacent the X-ray tube 2. In this embodiment, an irradiation field is set by controlling the collimator to emit X rays in a fan beam form diverging in the longitudinal direction (the direction of body axis z) and the transverse direction (direction perpendicular in a horizontal plane to the body axis z) of the patient M. The X-ray tube controller 7 controls the X-ray tube 2 to emit X rays (in the fan beam form) intermittently whenever the X-ray tube 2 and FPD 3 move every pitch (predetermined distance) described hereinafter. The FPD controller 5 controls the FPD 3 to detect X rays transmitted through the patient M irradiated intermittently.

The controller 10 has a central processing unit (CPU) and other elements. The memory 11 has storage media, typically a ROM (Read-Only Memory) and RAM (Random Access Memory). The input unit 12 has a pointing device, typically a mouse, keyboard, joy stick, trackball and/or touch panel.

The image processor 9 includes a correcting unit 9a for carrying out lag correction and gain correction on the X-ray detection signals and outputting X-ray images projected on the detecting plane of FPD 3, an image decomposing unit 9b for decomposing the corrected X-ray images for every pitch, an image composing unit 9c for composing the decomposed images for each projection angle to obtain a projection image for each projection angle, and a reconstruction processing unit 9d for carrying out a reconstruction process based on the composed projection images to obtain a sectional image. The image decomposing unit 9b corresponds to the image decomposing device in this invention. The image composing unit 9c corresponds to the image composing device in this invention. The reconstruction processing unit 9d corresponds to the reconstruction processing device in this invention. Specific functions of the image decomposing unit 9b, image composing unit 9c and reconstruction processing unit 9d will be described hereinafter with reference to FIGS. 6-8.

The memory 11 is constructed for writing and storing each image processed by the image processor 9. As does the controller 10, the FPD controller 5 and X-ray tube controller 7 also have CPUs and so on.

Figure 4:
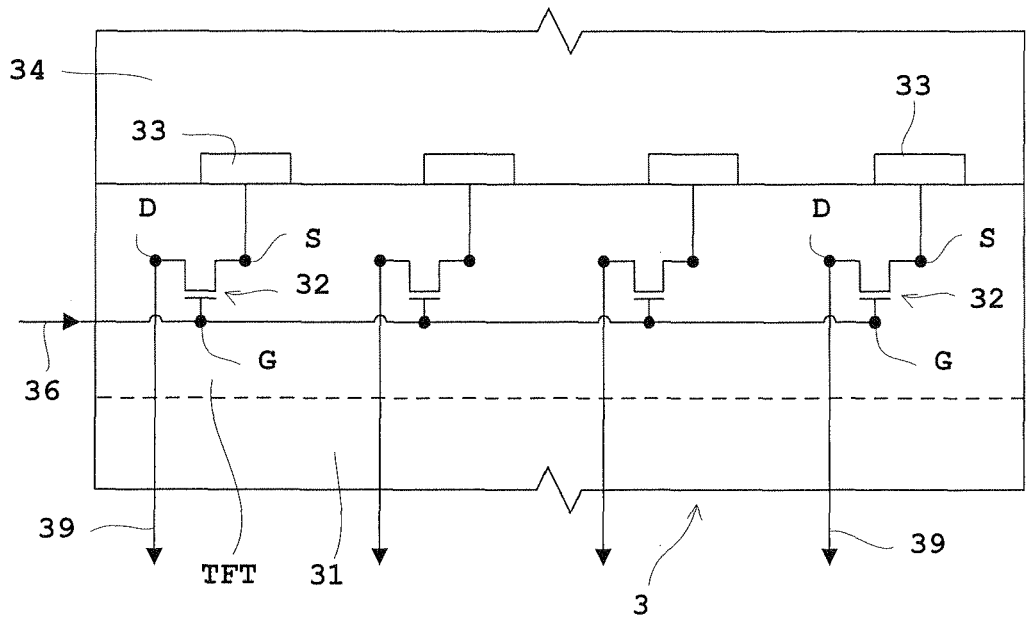
FIG. 4 is an equivalent circuit, seen in side view, of the flat panel X-ray detector (FPD)
Figure 5:
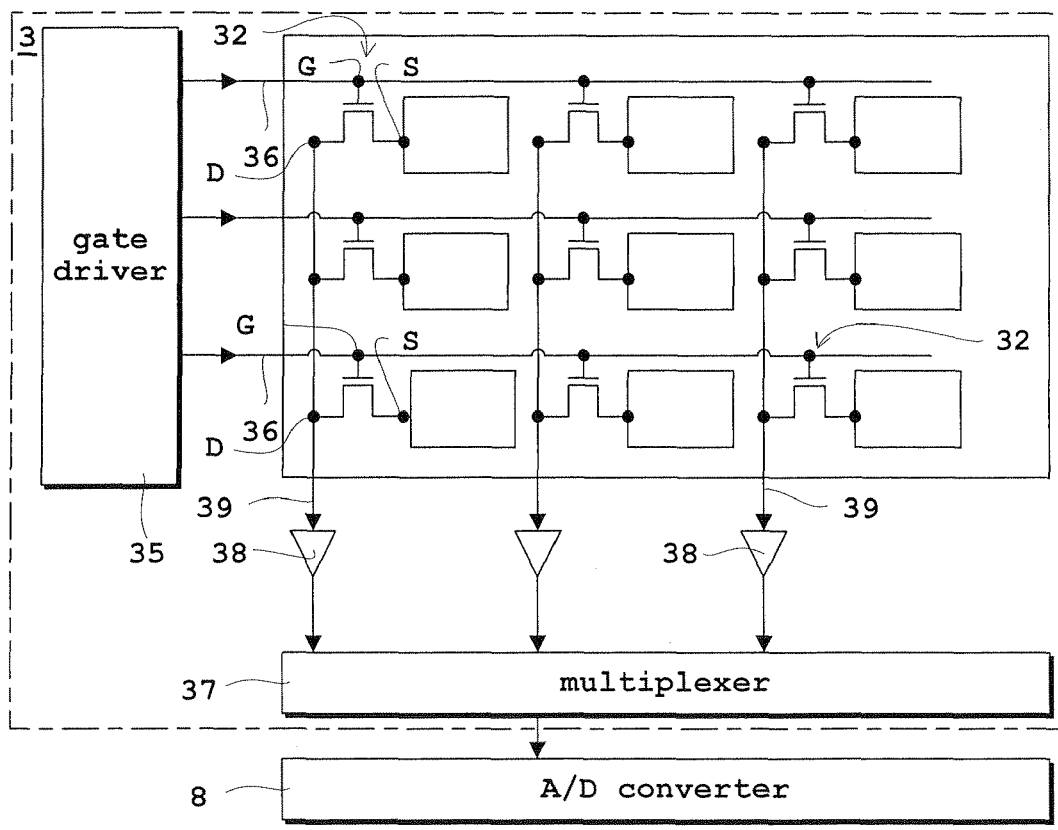
FIG. 5 is an equivalent circuit, seen in plan view, of the flat panel X-ray detector (FPD)

Next, the construction of the flat panel X-ray detector (FPD) 3 will be described with reference to FIGS. 4 and 5. FIG. 4 is an equivalent circuit, seen in side view, of the flat panel X-ray detector (FPD). FIG. 5 is an equivalent circuit, seen in plan view, of the flat panel X-ray detector (FPD).

As shown in FIG. 4, the FPD 3 includes a glass substrate 31, and thin film transistors TFT formed on the glass substrate 31. As shown in FIGS. 4 and 5, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 4, an X-ray sensitive semiconductor 34 is laminated on the carrier collecting electrodes 33. As shown in FIGS. 4 and 5, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 5, a plurality of data bus lines 39 are connected through amplifiers 38 to a multiplexer 37 for collecting charge signals and outputting as one. As shown in FIGS. 4 and 5, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X rays incident on the detecting plane through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signals, and outputs them as X-ray detection signals.

Figure 6:
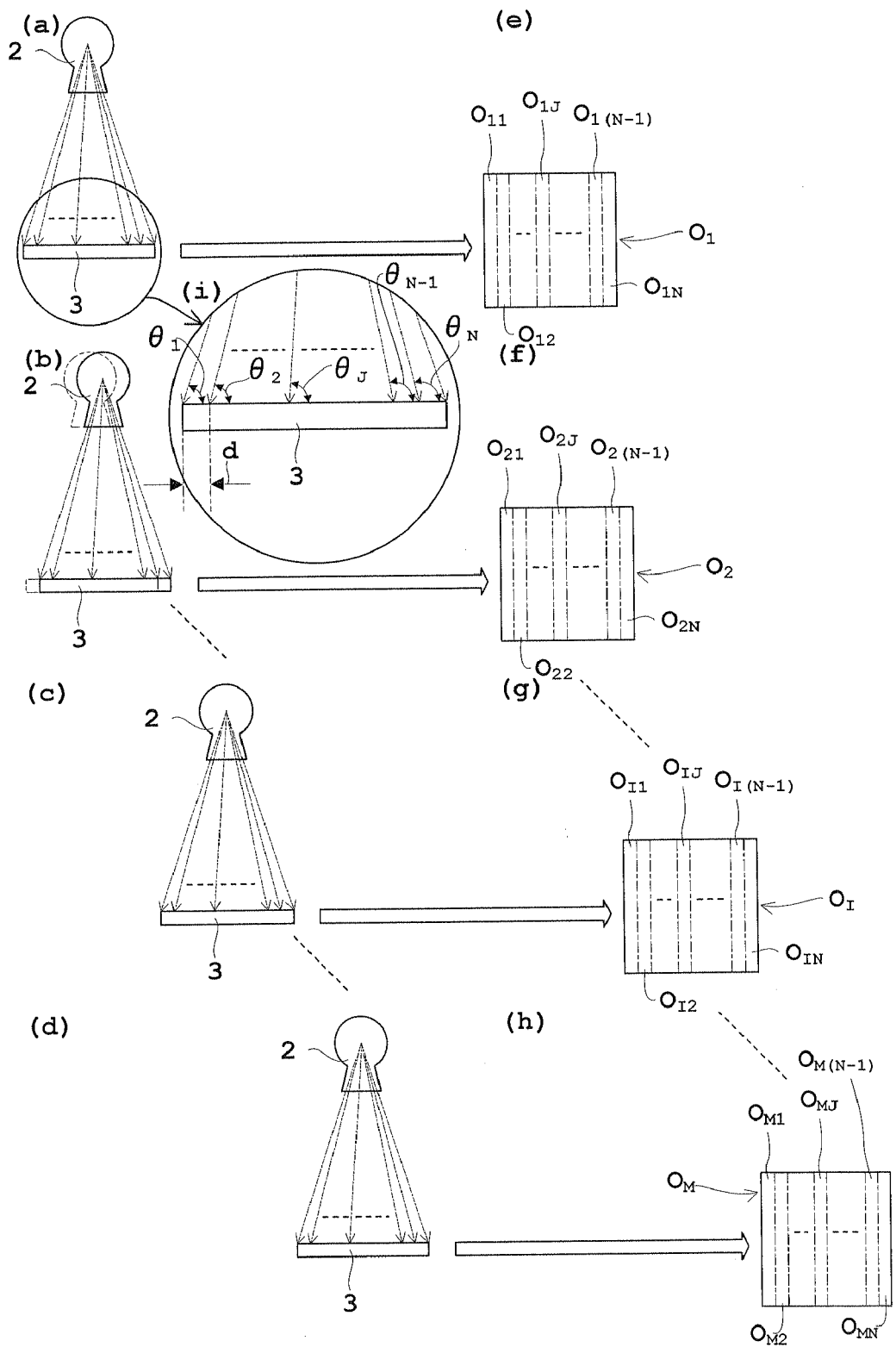
FIG. 6($a$)-($i$) are schematic views depicting for each pitch (predetermined distance) an image pickup principle by the X-ray tube and flat panel X-ray detector (FPD)
Figure 7:
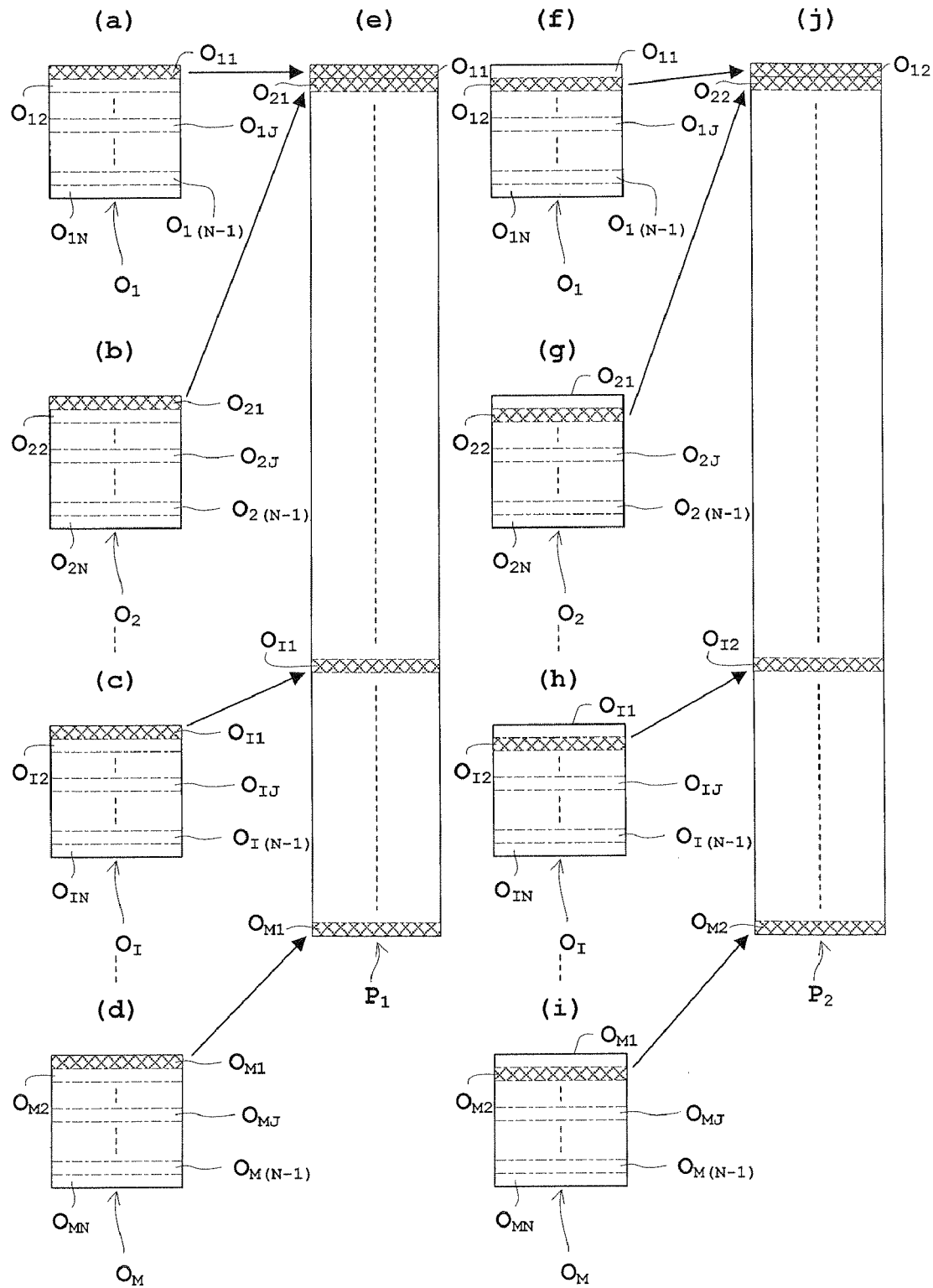
FIG. 7($a$)-($j$) are schematic views depicting separation of images and composition for projection images.
Figure 8:
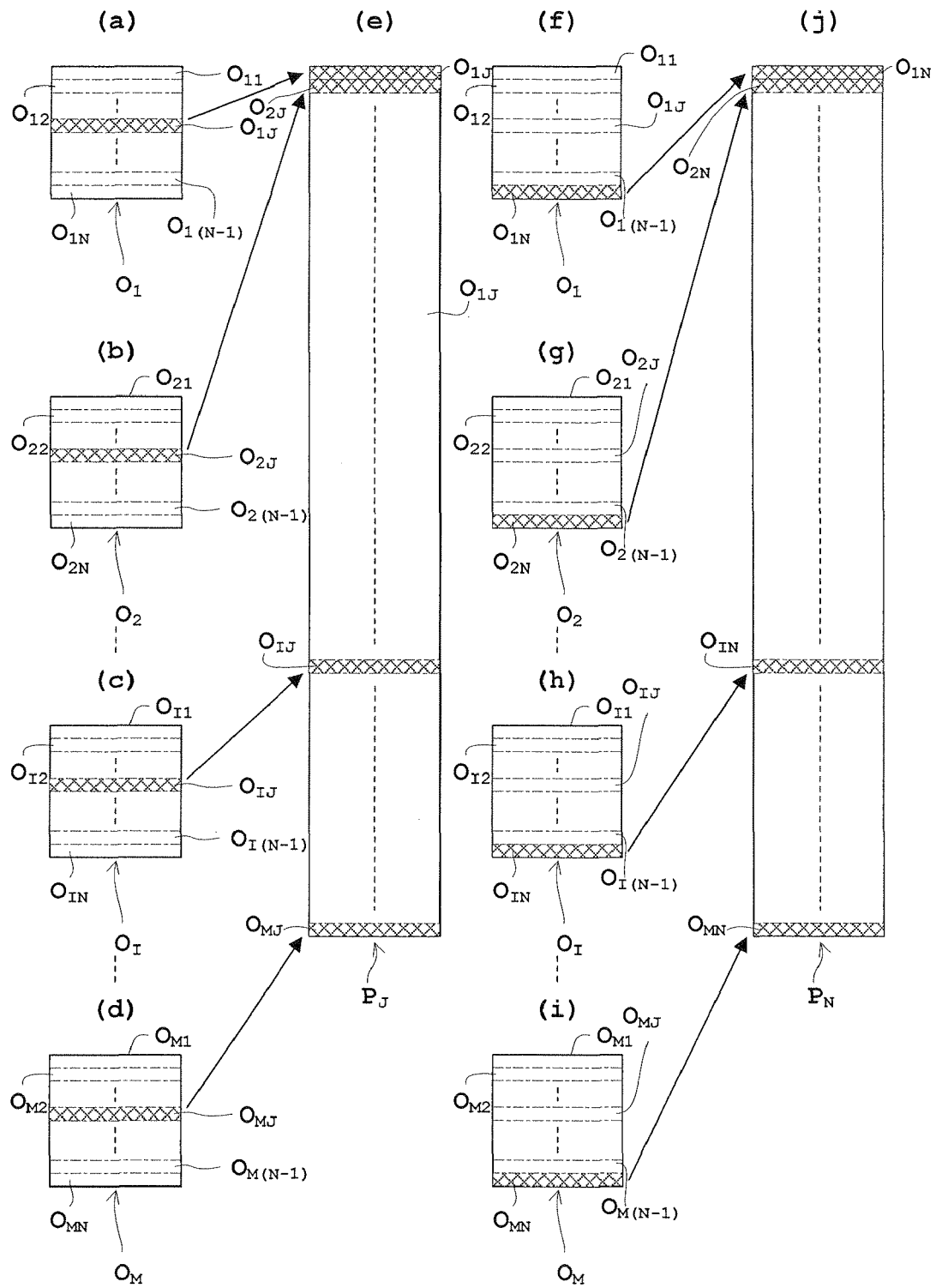
FIG. 8($a$)-($j$) are schematic views depicting separation of images and composition for projection images.

Next, specific functions of the image decomposing unit 9b, image composing unit 9c and reconstruction processing unit 9d will be described with reference to FIGS. 6-8. FIG. 6 is a schematic view depicting for every pitch (predetermined distance) an image pickup principle by the X-ray tube and flat panel X-ray detector (FPD). FIGS. 7 and 8 are schematic views depicting separation of images and composition for projection images. Description will be made assuming that X-ray images projected on the detecting plane of FPD 3 have already gone through the processes of lag correction and gain correction by the correcting unit 9a.

X-ray images projected on the detecting plane of FPD 3, as the X-ray tube 2 and FPD 3 move every pitch d as shown in FIGS. 6(a)-6(d), are referred to as $O_1, O_2, \ldots, O_I, \ldots,$ and $O_M$ as shown in FIGS. 6(e)-6(h) ($1 \leq I \leq M$). Whenever the X-ray tube 2 and FPD 3 move every pitch d, the X-ray tube 2 emits X rays intermittently. That is, with movement by every pitch d, X rays are emitted in pulse.

Specifically, when X rays are first emitted with the X-ray tube 2 and FPD 3 located in the position shown in FIG. 6(a), X rays are next emitted in the position shown in FIG. 6(b) after movement by pitch d. The FPD 3 detects the X rays in FIG. 6(a), to obtain X-ray image $O_1$ (see FIG. 6(e)). The FPD 3 detects X rays in FIG. 6(b), to obtain X-ray image $O_2$ (see FIG. 6(f)). Similarly thereafter, as the X-ray tube 2 and FPD 3 move every pitch d, X rays are emitted for the (I−1)th time in the position shown in FIG. 6(c), and the FPD 3 detects the X rays in FIG. 6(c), to obtain X-ray image $O_I$ (see FIG. 6(g)). Finally, X rays are emitted for the (M−1)th in the position shown in FIG. 6(d), and the FPD 3 detects the X rays in FIG. 6(d), to obtain X-ray image $O_M$ (see FIG. 6(h)). In this embodiment, the image pickup start position in FIG. 6(a) is the head of the patient M, the image pickup end position in FIG. 6(d) is the feet of the patient M, and movement is made in order from the head to the feet with the movement of the X-ray tube 2 and FPD 3 as in FIGS. 6(a)-6(d).

With the X-ray tube 2 and FPD 3 moving every pitch d, the image decomposing unit 9b can decompose X-ray images $O_1, O_2, \ldots, O_I, \ldots,$ and $O_M$ at every pitch d. Specifically, as shown in the enlarged view of FIG. 6(i), projection angles which are angles between the radiation axis from the X-ray tube 2 to the FPD 3 and the body axis z of the patient are referred to as $\theta_1, \theta_2, \ldots, \theta_J, \ldots, \theta_{N-1}$ and $\theta_N$ for every pitch d ($1 \leq J \leq N$). Then, the images decomposed at every pitch d coincide with images divided into the same projection angles $\theta_1, \theta_2, \ldots, \theta_{N-1}$ and $\theta_N$, respectively.

As shown in FIG. 6(e), X-ray image $O_1$ is decomposed at every pitch d into $O_{11}, O_{12}, \ldots, O_{1J}, \ldots, O_{1(N-1)}$ and $O_{1N}$. Decomposed image $O_{11}$ is an image obtained from an emission at projection angle $\theta_1$. Decomposed image $O_{12}$ is an image obtained from an emission at projection angle $\theta_2$. Similarly thereafter, decomposed image $O_{1J}$ is an image obtained from an emission at projection angle $\theta_J$. Finally, decomposed image $O_{1N}$ is an image obtained from an emission at projection angle $\theta_N$.

Similarly, as shown in FIG. 6(f), X-ray image $O_2$ is decomposed at every pitch d into $O_{21}, O_{22}, \ldots, O_{2J}, \ldots, O_{2(N-1)}$ and $O_{2N}$. Decomposed image $O_{21}$ is an image obtained from the emission at projection angle $\theta_1$. Decomposed image $O_{22}$ is an image obtained from the emission at projection angle $\theta_2$. Similarly thereafter, decomposed image $O_{2J}$ is an image obtained from the emission at projection angle $\theta_J$. Finally, decomposed image $O_{2N}$ is an image obtained from the emission at projection angle $\theta_N$.

At the (I−1)th time, as shown in FIG. 6(g), X-ray image $O_I$ is decomposed at every pitch d into $O_{I1}, O_{I2}, \ldots, O_{IJ}, \ldots, O_{I(N-1)}$ and $O_{IN}$. Decomposed image $O_{I1}$ is an image obtained from the emission at projection angle $\theta_1$. Decomposed image $O_{I2}$ is an image obtained from the emission at projection angle $\theta_2$. Similarly thereafter, decomposed image $O_{IJ}$ is an image obtained from the emission at projection angle $\theta_J$. Finally, decomposed image $O_{IN}$ is an image obtained from the emission at projection angle $\theta_N$.

Finally, at the (M−1)th time, as shown in FIG. 6(h), X-ray image $O_I$ is decomposed at every pitch d into $O_{M1}, O_{M2}, O_{MJ}, O_{M(N-1)}$ and $O_{MN}$. Decomposed image $O_{M1}$ is an image obtained from the emission at projection angle $\theta_1$. Decomposed image $O_{M2}$ is an image obtained from the emission at projection angle $\theta_2$. Similarly thereafter, decomposed image $O_{MJ}$ is an image obtained from the emission at projection angle $\theta_J$. Finally, decomposed image $O_{MN}$ is an image obtained from the emission at projection angle $\theta_N$.

The image composing unit 9c composes the images decomposed in this way, for each of the same projection angles $\theta_1, \theta_2, \ldots, \theta_J, \ldots, \theta_{N-1}$ and $\theta_N$ as shown in FIGS. 7 and 8. As described above, the respective X-ray images $O_1, O_2, \ldots, O_I, \ldots,$ and $O_M$ have decomposed images (that is, divided into the projection angles $\theta_1, \theta_2, \ldots, \theta_J, \ldots, \theta_{N-1}$ and $\theta_N$) for each pit d as shown in FIGS. 7(a)-7(d), FIGS. 7(f)-7(i), FIGS. 8(a)-8(d), and FIGS. 8(f)-8(i).

In the case of projection angle $\theta_1$, for example, image $O_{11}$ in X-ray image $O_1$ shown in FIG. 7(a), image $O_{21}$ in X-ray image $O_2$ shown in FIG. 7(b), . . . , image $O_{I1}$ in X-ray image $O_I$ shown in FIG. 7(c), . . . , and image $O_{M1}$ in X-ray image $O_M$ shown in FIG. 7(d) are composed to obtain projection image $P_1$ for projection angle $\theta_1$ as shown in FIG. 7(e).

Similarly, in the case of projection angle $\theta_2$, image $O_{12}$ in X-ray image $O_1$ shown in FIG. 7(f), image $O_{22}$ in X-ray image $O_2$ shown in FIG. 7(g), . . . , image $O_{I2}$ in X-ray image $O_I$ shown in FIG. 7(h), . . . , and image $O_{M2}$ in X-ray image $O_M$ shown in FIG. 7(i) are composed to obtain projection image $P_2$ for projection angle $\theta_2$ as shown in FIG. 7(j).

At the (J-1)th time, in the case of projection angle $\theta_J$, image $O_{1J}$ in X-ray image $O_1$ shown in FIG. 8(a), image $O_{2J}$ in X-ray image $O_2$ shown in FIG. 8(b), . . . , image $O_{IJ}$ in X-ray image $O_I$ shown in FIG. 8(c), . . . , and image $O_{MJ}$ in X-ray image $O_M$ shown in FIG. 8(d) are composed to obtain projection image $P_J$ for projection angle $\theta_J$ as shown in FIG. 8(e).

Finally, at the (N-1)th time, in the case of projection angle $\theta_N$, image $O_{1N}$ in X-ray image $O_1$ shown in FIG. 8(f), image $O_{2N}$ in X-ray image $O_2$ shown in FIG. 8(g), . . . , image $O_{IN}$ in X-ray image $O_I$ shown in FIG. 8(h), . . . , and image $O_{MN}$ in X-ray image $O_M$ shown in FIG. 8(i) are composed to obtain projection image $P_N$ for projection angle $\theta_N$ as shown in FIG. 8(j).

To summarize the above, the image composing unit 9c composes the decomposed images for each of the same projection angles $\theta_1, \theta_2, \ldots, \theta_J, \ldots, \theta_{N-1}$ and $\theta_N$ to obtain projection images $P_1, P_2, \ldots, P_J, \ldots,$ and $P_N$ for the respective projection angles $\theta_1, \theta_2, \ldots, \theta_J, \ldots, \theta_{N-1}$ and $\theta_N$ as shown in FIGS. 7(e), 7(j), 8(e) and 8(j).

The reconstruction processing unit 9d carries out a reconstruction process based on the composed projection images $P_1, P_2, \ldots, P_J, \ldots,$ and $P_N$ to obtain a sectional image.

The reconstruction process may be carried out with the Feldkamp method using the well-known filtered back projection (FBP) (also called "filter-corrected back projection"). The Feldkamp method will be described hereinafter with reference to FIGS. 9-19.

Where the number of projection images $P_1, P_2, \ldots, P_J, \ldots,$ and $P_N$ is N [Frames], the moving speed of the imaging system such as the X-ray tube 2 and FPD 3 is v [mm/sec], the view size of FPD 3 is V[mm], and the image pickup cycle (called "pulse time width") is T [sec/Frame], the moving speed v [mm/sec] is expressed by v[mm/sec]=V [mm]/N[Frame]×1/T [sec/Frame]. The inverse of the image pickup cycle is image pickup speed, and where the image pickup speed is F [Frame/sec], the moving speed v [mm/sec] is expressed also by v[mm/sec]=V[mm]/N[Frame]×F [Frame/sec]. Pitch d [mm] is expressed by d [mm]=V[mm]/N [Frames].

Where, for example, view size V used in this embodiment is 17 inches (=430 [mm]), the number N of projection images $P_1, P_2, \ldots, P_J, \ldots,$ and $P_N$ is 50 [Frames], and the image pickup speed F is 15 [Frames/sec], the moving speed v is v=[mm/sec]=430 [mm]/50 [Frames]×15 [Frames/sec]=129 [mm/sec], and pitch d is 430 [mm]/50 [Frames]=8.6 [mm/Frame]. Therefore, the X-ray tube 2 and FPD 3 are moved parallel to each other at the same speed of 129 [mm/sec], and X rays are emitted intermittently with the timing of image pickup speed 15 [Frame/sec], whereby X rays are emitted intermittently from the X-ray tube 2 as the X-ray tube 2 and FPD 3 move every pitch 8.6 [mm/Frame]. And 50 projection images $P_1, P_2, \ldots, P_J, \ldots,$ and $P_{50}$ can be obtained. Further, the longer distance the X-ray tube 2 and FPD 3 move, the longer becomes the area of each of the projection images $P_1, P_2, \ldots, P_J, \ldots,$ and $P_N$ as shown in FIGS. 7 and 8.

Figure 10:
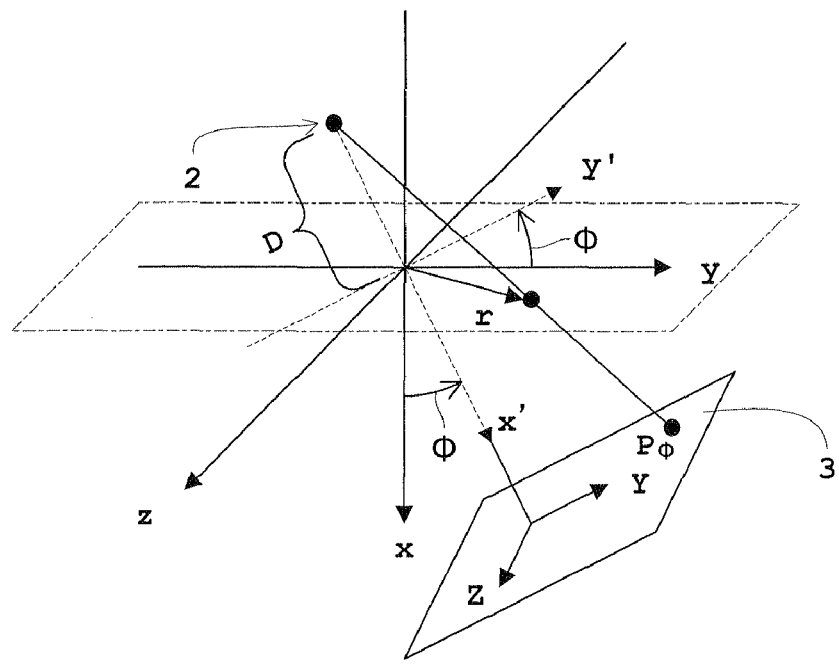
FIG. 10 is a schematic view illustrating the Feldkamp algorithm according to the embodiment.
Figure 11:
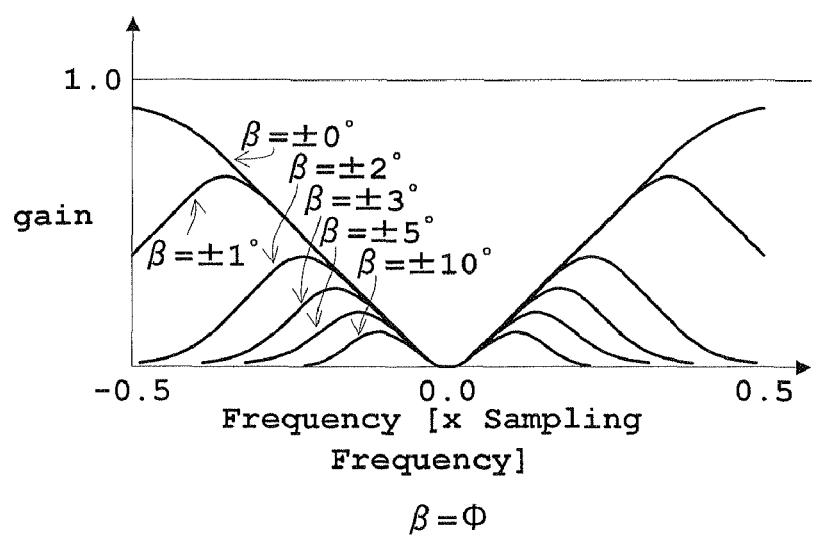
FIG. 11 is a characteristic view of a filter function.
Figure 12:
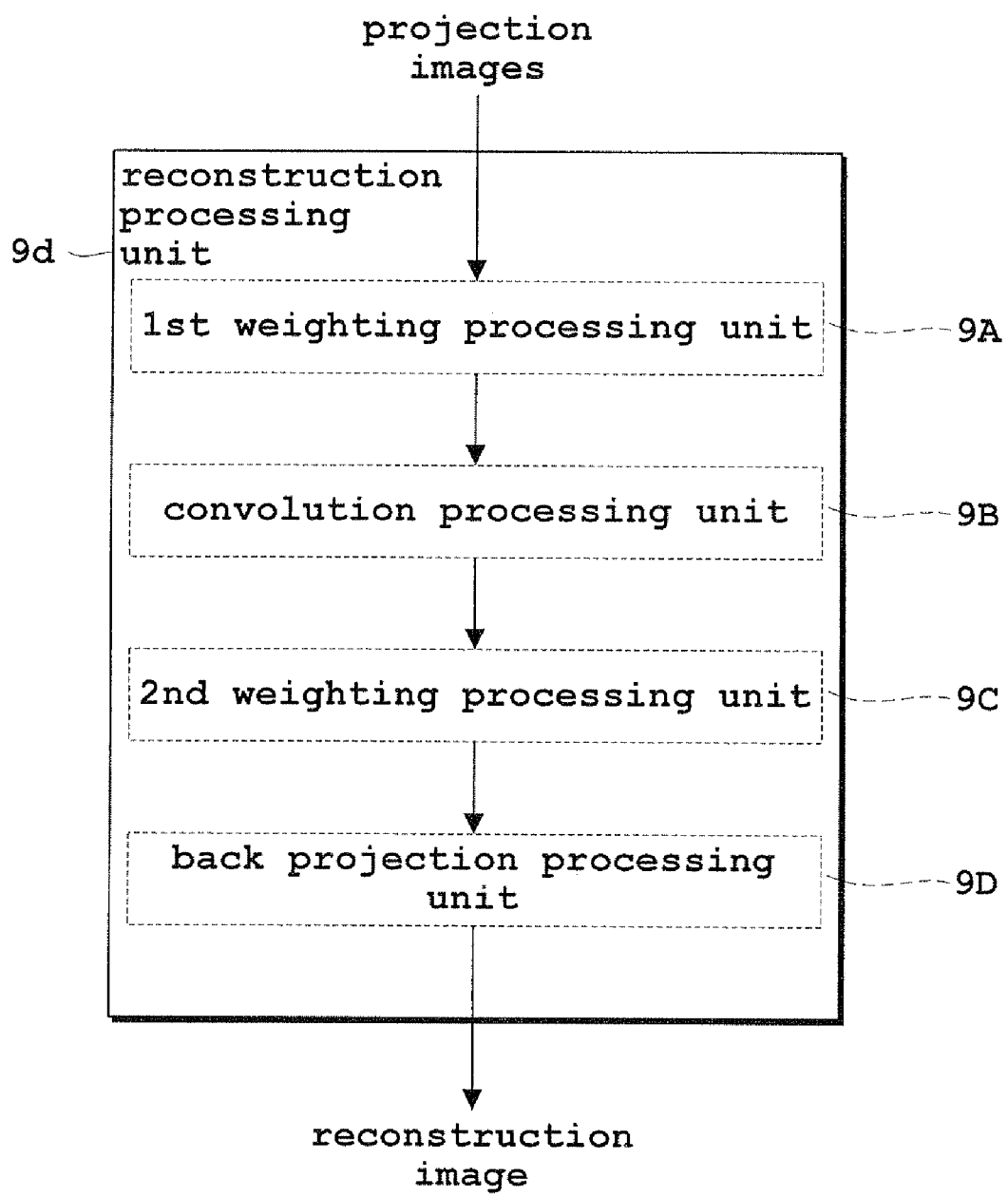
FIG. 12 is a block diagram of a reconstruction processing unit according to the embodiment and a schematic view showing a flow of data.
Figure 14:
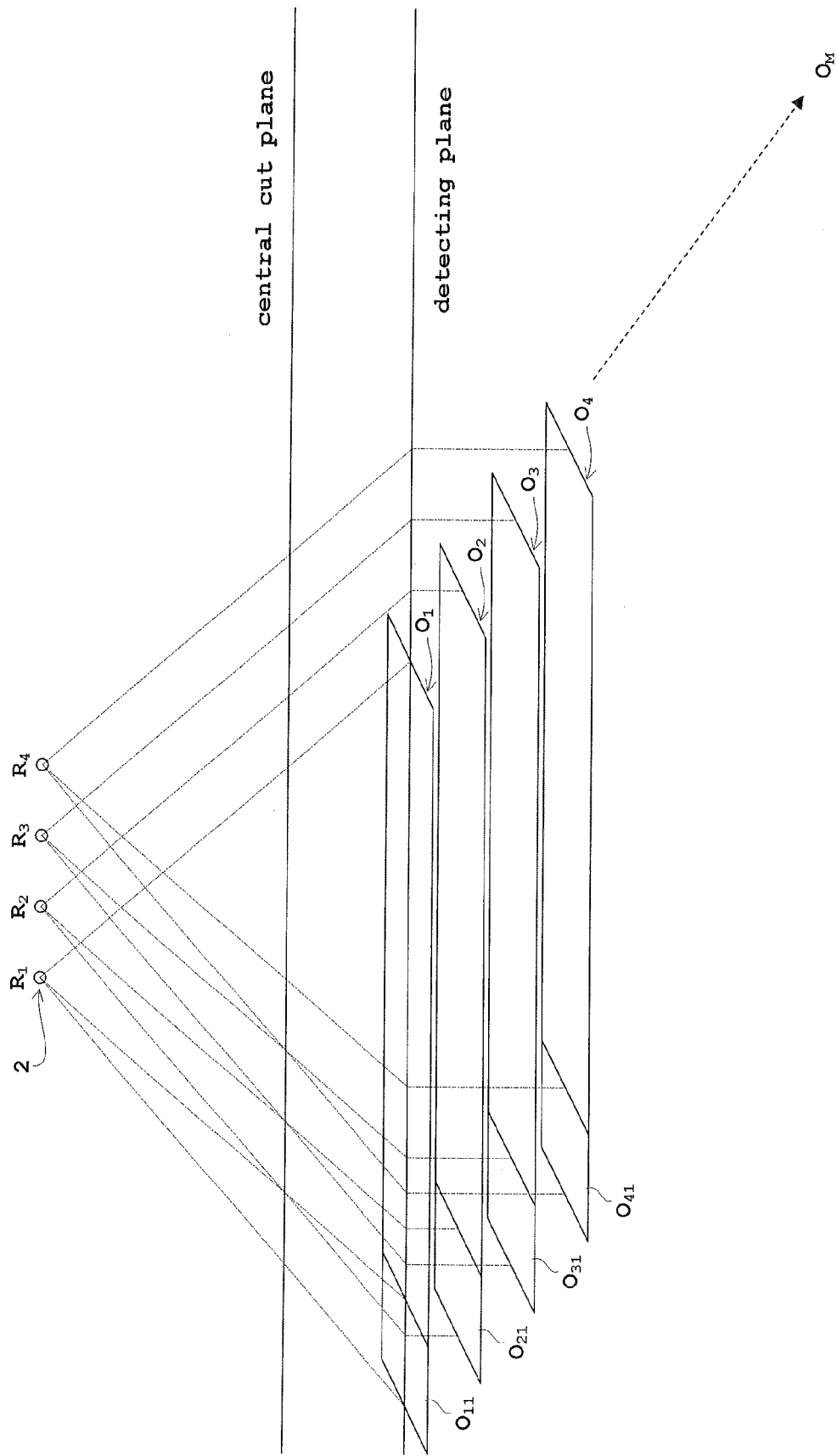
FIG. 14 is a schematic view showing a relationship between an image of a common projection angle of each X-ray emission and a projection image for illustrating a method of applying Feldkamp to long X-ray images.
Figure 15:
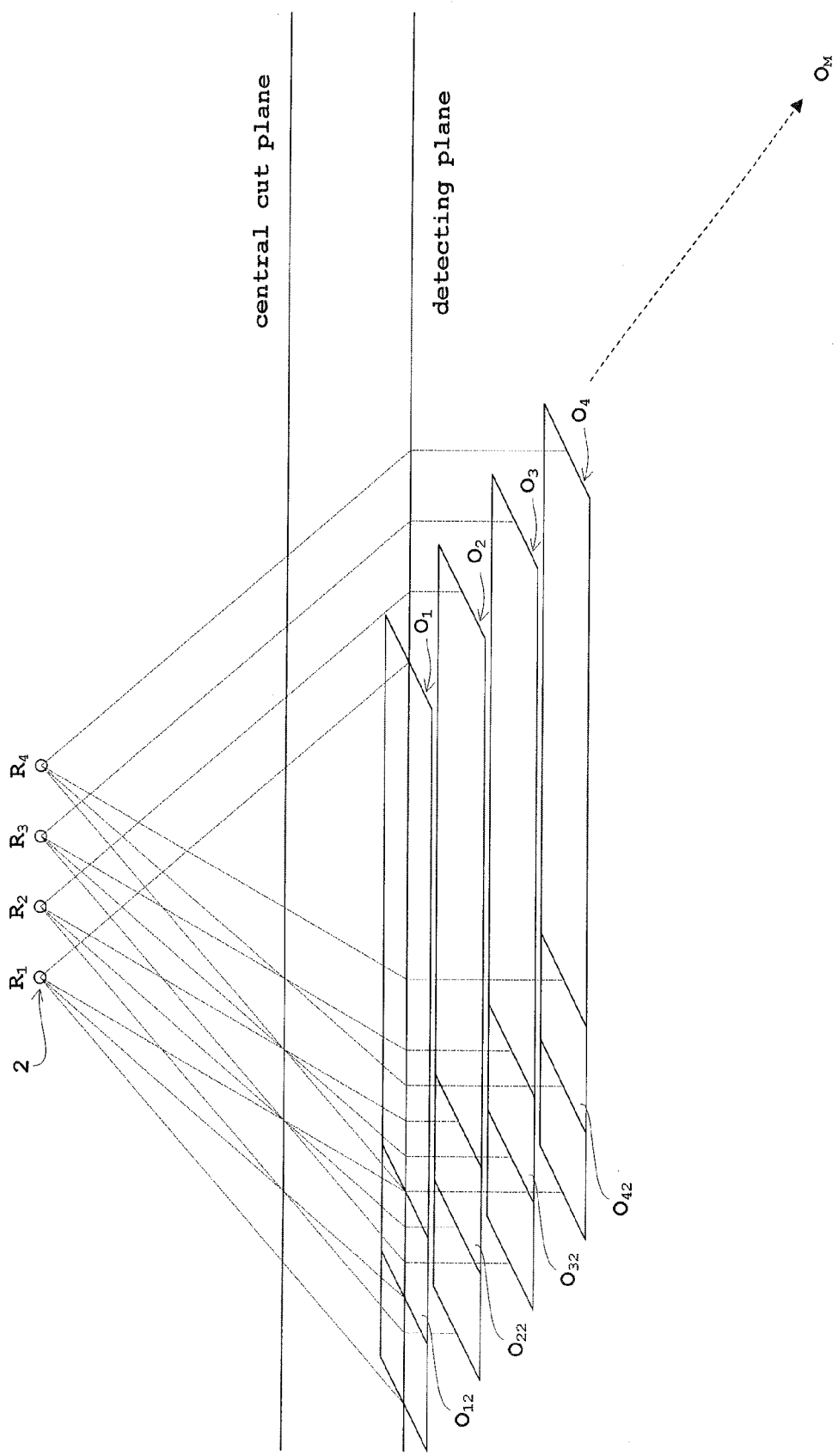
FIG. 15 is a schematic view showing a relationship between an image of a common projection angle of each X-ray emission and a projection image for illustrating a method of applying Feldkamp to long X-ray images.
Figure 16:
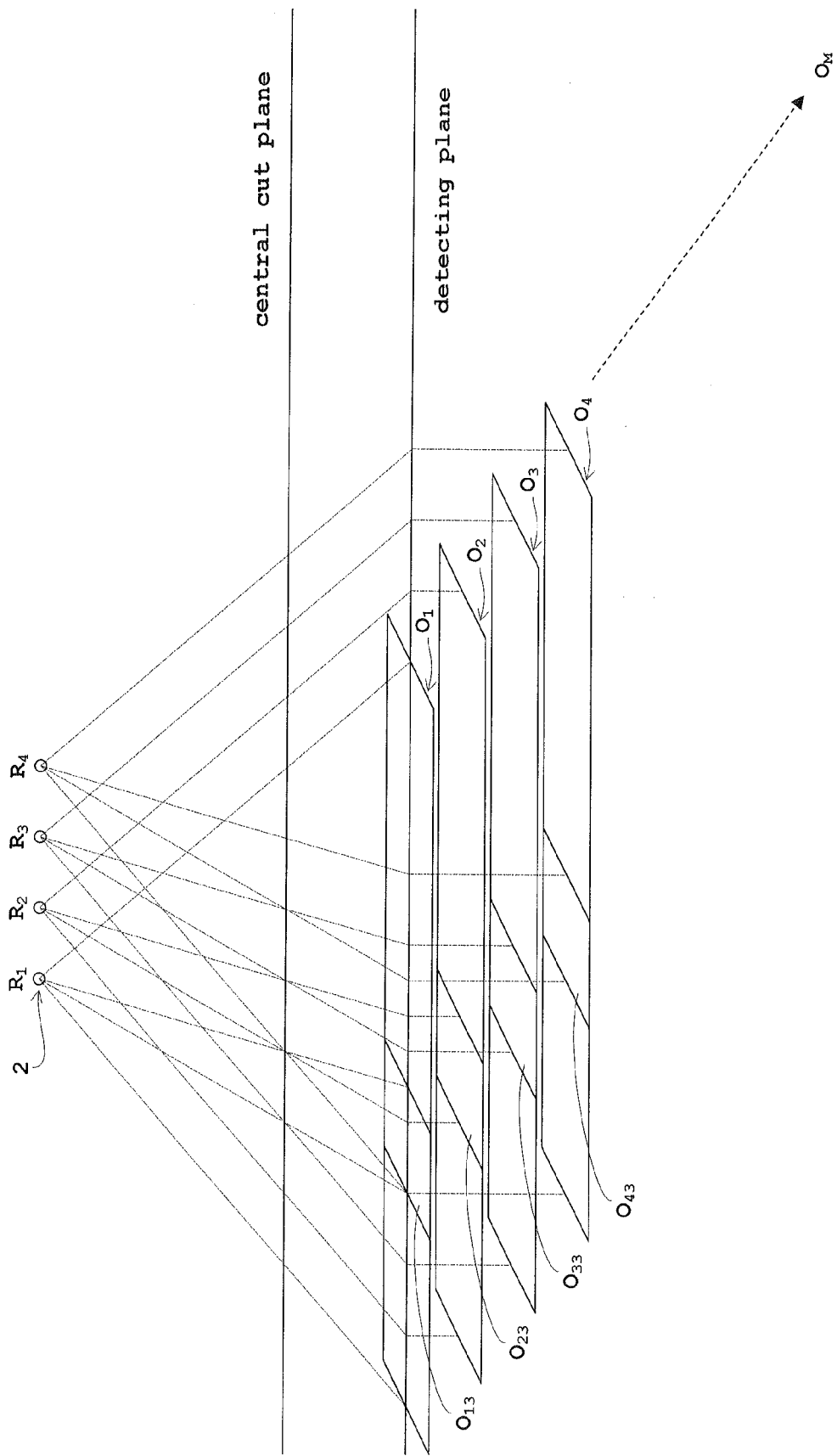
FIG. 16 is a schematic view showing a relationship between an image of a common projection angle of each X-ray emission and a projection image for illustrating a method of applying Feldkamp to long X-ray images.
Figure 17:
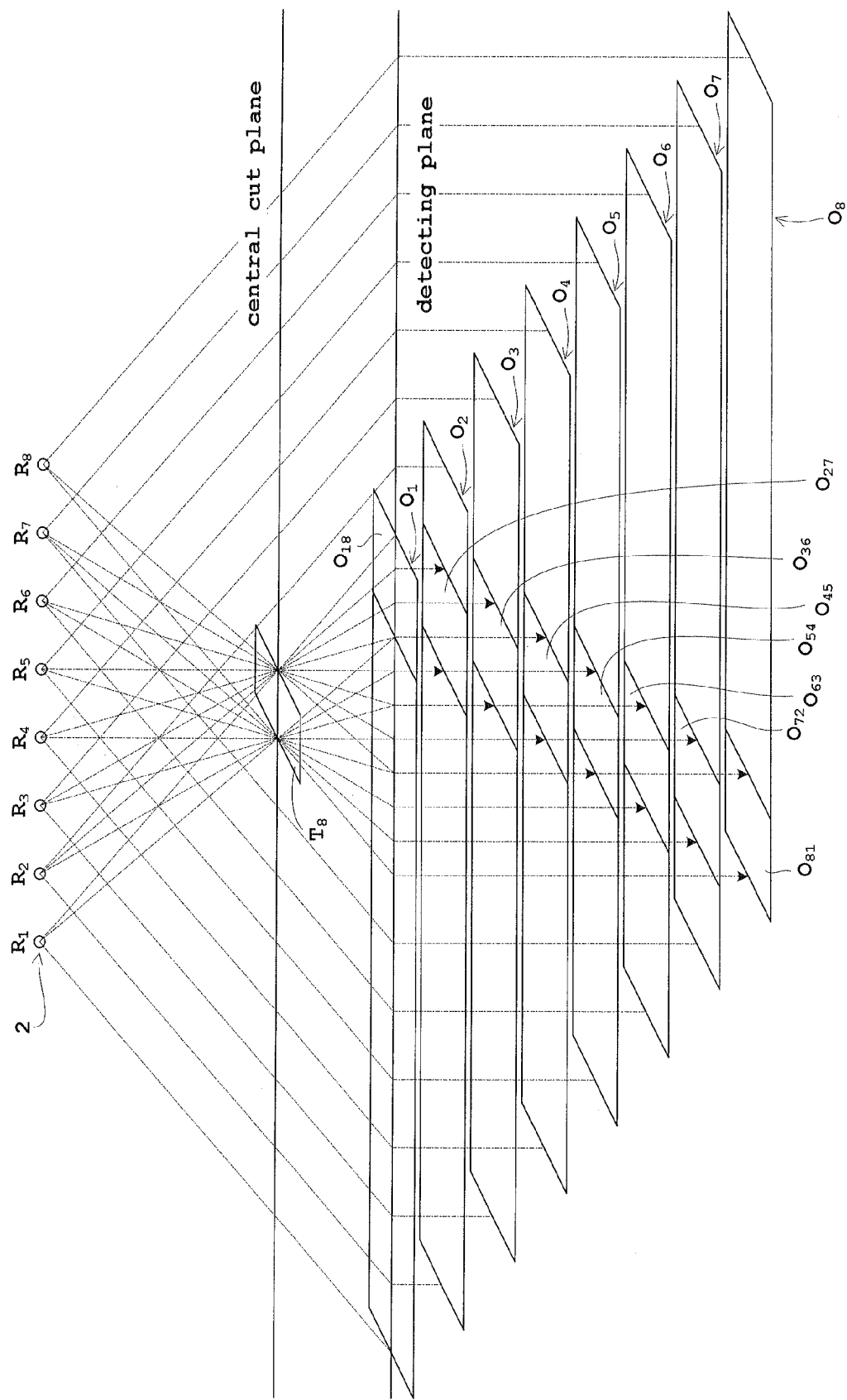
FIG. 17 is a schematic view showing a relationship between each cut plane and projection image where N=8 for illustrating a method of applying Feldkamp to long X-ray images.
Figure 18:
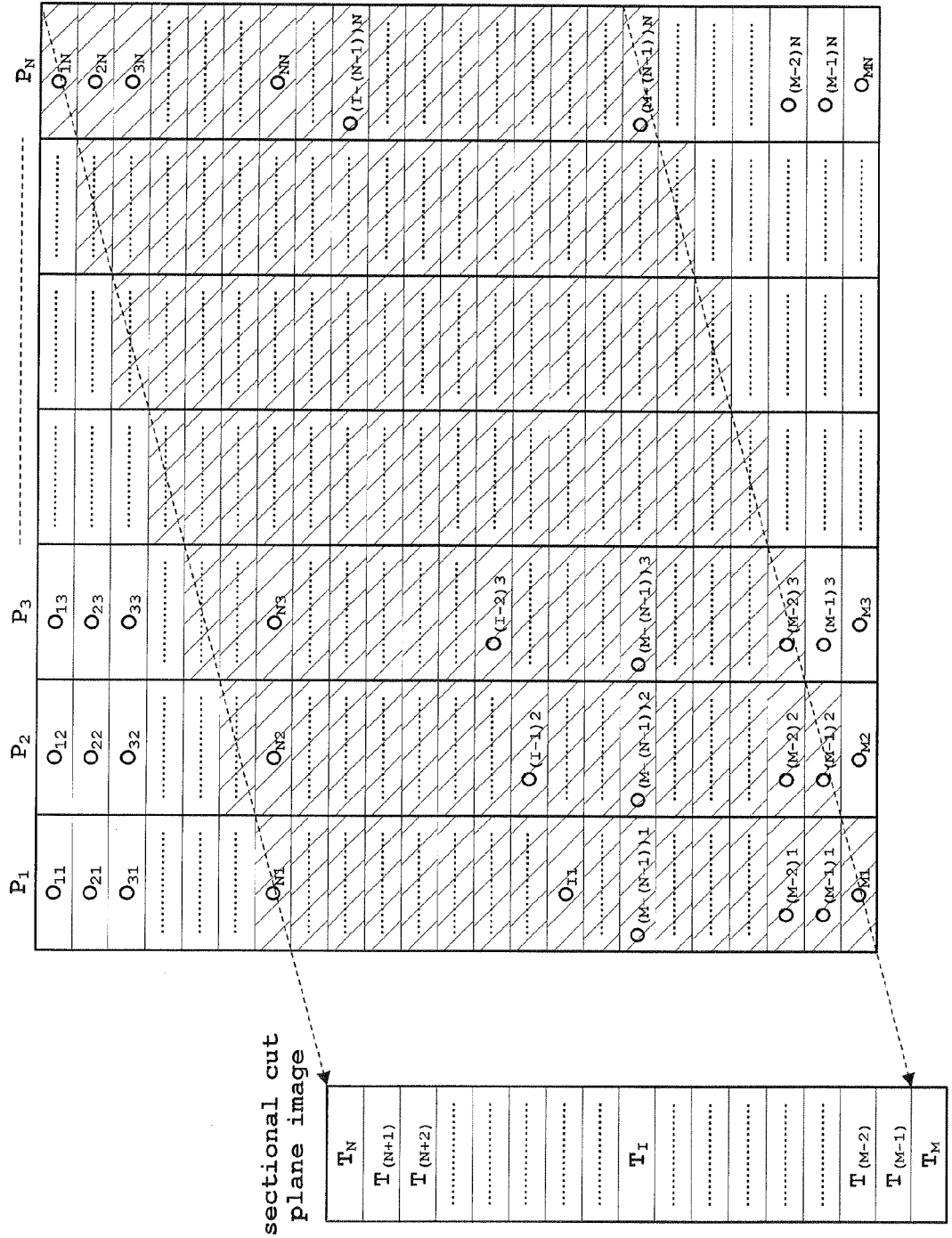
FIG. 18 is a schematic view showing a relationship between cut plane and projection image for illustrating a method of applying Feldkamp to long X-ray images.
Figure 19:
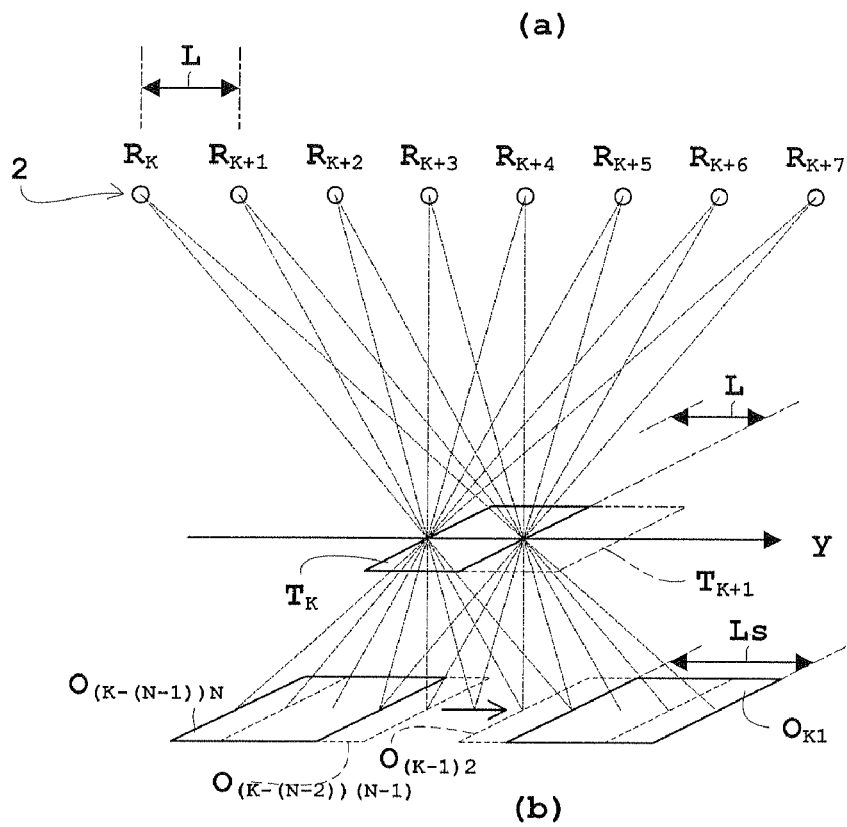
FIG. 19($a$) and ($b$) are schematic views showing a relationship between cut plane and projection image for illustrating a method of applying Feldkamp to long X-ray images.
Figure 20:
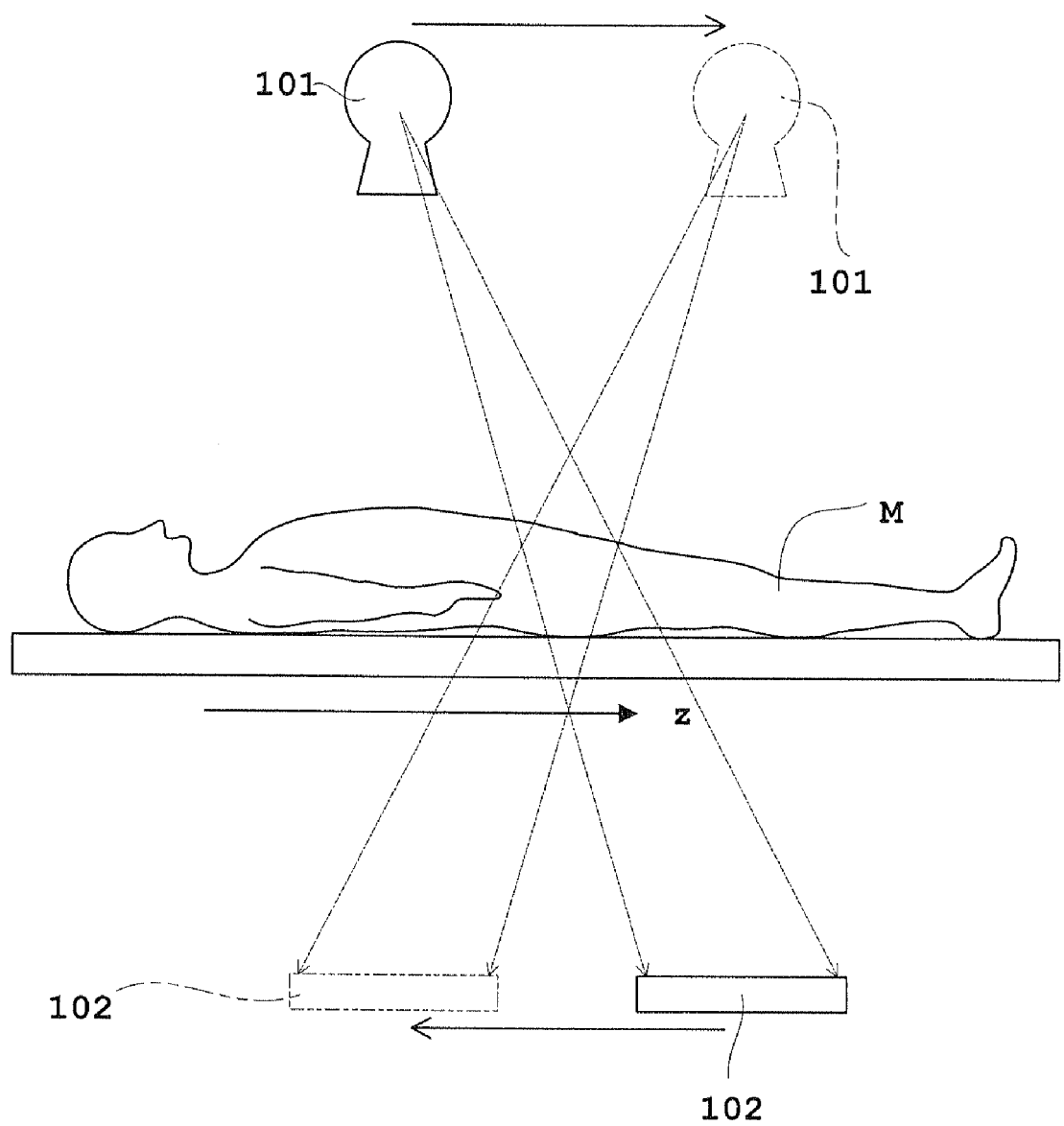
FIG. 20 is a side view showing an outline of a conventional X-ray body section imaging apparatus.

Next, a specific technique in the case of applying this embodiment to the Feldkamp method will be described with reference to FIGS. 9-19. FIG. 9(a) is a schematic view of arcuate track body section radiography. FIG. 9(b) is a schematic view of linear track body section radiography. FIG. 10 is a schematic view illustrating the Feldkamp algorithm according to the embodiment. FIG. 11 is a characteristic view of a filter function. FIG. 12 is a block diagram of the reconstruction processing unit according to the embodiment and a schematic view showing a flow of data. FIG. 13 is a schematic view illustrating a method of applying Feldkamp to linear track body section radiography. FIGS. 14-16 are schematic views showing a relationship between an image of a common projection angle of each X-ray emission and a projection image for illustrating a method of applying Feldkamp to long X-ray images. FIG. 17 is a schematic view showing a relationship between each cut plane and projection image where N=8 for illustrating a method of applying Feldkamp to long X-ray images. FIG. 18 is a schematic view showing a relationship between cut plane and projection image for illustrating a method of applying Feldkamp to long X-ray images. FIG. 19 is a schematic view showing a relationship between cut plane and projection image for illustrating a method of applying Feldkamp to long X-ray images. While the body axis was z in FIG. 20 and FIGS. 1-8, FIGS. 9-19 will be described with the body axis as y because of the representation of 3D coordinates in the Feldkamp method.

The Feldkamp method is used for the sectional image reconstruction method used in cone beam CT. Although this is applied to the arcuate track body section radiography shown in FIG. 9(a), it is extensible also to the linear track body section radiography shown in FIG. 9(b). First of all, a reconstruction method of the arcuate track body section by the Feldkamp method will be described. The extension to the linear track body section will be described next.

(I) Arcuate Track Body Section Radiography

The reconstruction algorithm by the Feldkamp method is expressed as the following equation (1)-equation (3). How to plot coordinates is shown in FIG. 10. Coordinates x, y and z are a coordinate system fixed to space. The imaging system including the X-ray tube 2 and FPD 3 rotates about the axis of this z-axis. That is, the X-ray tube 2 makes a circular motion with radius D about the origin on x-y plane.

[Numeric 1]

$$f(r) = \frac{1}{4\pi^2} \int W_2 \int g_y(Y(r)-Y')P_\theta(Y', Z(r))W_1 dY' d\phi \quad (1)$$

$\underbrace{\phantom{xxxxx}}_{\text{convolution}}$
$\underbrace{\phantom{xxxxxxxxx}}_{\text{correction of beam spread influence}}$
$\underbrace{\phantom{xxxxxxxxxxxxxxxxx}}_{\text{back projection}}$ $$W_1 = \frac{D}{(D^2 + Y'^2 + Z^2)^{1/2}} \quad (2)$$

$$W_2 = \frac{D^2}{(D + r \cdot x')^2} \quad (3)$$

Here, $g_y$ is a filter for reducing obstructive shadows (flow images) occurring in Y-direction at a time of reconstructing a sectional image, and an example thereof is shown in FIG. 11. However, while the projection angle was $\theta$ in FIGS. 1-8, FIGS. 9-19 will be described with the projection angle as $\phi$ because of the representation of the algorithm in the Feldkamp method. In FIG. 11, projection angle $\phi=\beta$. The term $W_1$ $(=D/(D^2+Y'^2+Z^2)^{1/2})$ in equation (1) and equation (2) above is given for correction of changes in pixel values caused by the cone beam effect.

The integral equation of f(r), when point r in 3D coordinate space is fixed, adds pixel values of coordinates of this point reflected on the projection image at each angle φ. Paradoxically speaking, the projection image is back-projected to the 3D coordinate space, and is added to the 3D coordinate space. However, because of the cone beam effect, the pixel values need to be corrected by an amount corresponding to the term $W_2$ ($=D^2/(D+r \cdot x')^2$) in the above equation (1) and equation (3).

FIG. 12 shows a block diagram of components of the reconstruction processing unit 9d (see FIG. 1 also) for carrying out the above processes, and a flow of data. Specifically, a first weighting processing unit 9A weights the projection data with $W_1$, a convolution processing unit 9B carries out convolution (convolution integral) thereof by filter function $g_y$, a second weighting processing unit 9C weights it with $W_2$, and a back projection processing unit 9D carries out back projection thereof to acquire a reconstruction image (i.e. sectional image).

(II) Application to Linear Track Body Section Radiography

In the Feldkamp method which is a reconstruction technique of cone beam CT, a perpendicular extending down from the X-ray tube 2 during rotation is at right angles to the detecting plane of FPD 3 as shown in FIG. 9(a). However, in the linear track body section, as shown in FIG. 9(b) and FIG. 13(b), the center of the cone beam-like X-ray beam emitted from the X-ray tube 2 passes through the center C of a certain sectional plane, and does not always impinge at right angles on the center of the detecting plane of FPD 3. That is, the angle of incidence on the central point of the detecting plane of FPD 3 is a different angle for each view, and therefore the Feldkamp method cannot directly be applied in this state.

Thus, as shown in FIG. 13(b), an imaginary rotation center axis VC refers to an axis that extends perpendicular to a straight line along which the center of the X-ray beam strikes at right angles the central point on the detecting plane of FPD 3, extends perpendicular to the moving direction of the X-ray tube 2 and FPD 3, and passes through a sectional plane substantially centrally of an area of interest of the patient M. A first perpendicular from the X-ray tube 2 to the central point of the detecting plane of FPD 3 is assumed to have a length SID. And a distance along this from the X-ray tube 2 to the center C of a particular sectional plane is set to SOD (=D). The length of a second perpendicular from the central point of FPD 3 in each view to the first perpendicular noted above is set to YA. Then, the length YA of the second perpendicular is expressed by the following equation (4):

$$YA = SID \cdot \tan \phi \quad (4)$$

Therefore, when carrying out back projection of each view, Y(r) is changed according to YA=SID·tan φ (written "SID*tan φ" in FIG. 13) each time to correspond to this imaginary rotation center axis VC. By carrying out the reconstruction process in this way, the Feldkamp method can be applied without working on the X-ray image which is the source image.

The above change of Y(r) will be described specifically. Regarding the imaginary rotation center axis VC as a reference in the space of the patient M, as to the same point of the patient M, the point indicated by vr (called "r vector") for B' in FIG. 13(b) and the point indicated by vrc (called "rc vector") for C' are considered the same point. Regarding the imaginary rotation center axis VC as a reference, the relationship in Y coordinates between the above two points is expressed as the following (5).

$$rc_y = r_y + SOD \cdot \tan \phi \quad (5)$$

where $rc_y$ is a length from VC to vrc, which is the length of r vector (SOD·tan φ is written as "D*tan φ" in FIG. 13).

And Y coordinates (based on VC) of the point where the X ray having passed vrc from the X-ray tube 2 is projected on the detecting plane of FPD 3 are set to Yc(r). Since the actual FPD 3 is considered to shift by YA=SID·tan φ, the coordinates on the detecting plane of actual FPD 3 are expressed by the following equation (6):

$$Y(r) = Yc(r) - SID \cdot \tan \phi \quad (6)$$

where Yc(r) is expressed as Yc(r)=SID·$rc_y$/SOD.

Thus, when carrying out back projection of each view, the reconstruction process may be carried out about each pixel only by changing parameter Y(r) in the above equation (1) based on the above equation (6) (that is, carrying out a coordinate correction). The Feldkamp method can be applied without modifying the data of the source image. The description has been made so far with reference to "Japanese Patent No. 3926574".

(III) Application to Long Tomosynthesis

FIGS. 14-16 show a positional relationship in which images with fixed projection angles of X-ray emission appear as X-ray images $O_1, O_2, \ldots, O_I, \ldots$, and $O_M$ (also see FIGS. 6-8). Assuming that a moving distance of the X-ray tube 2 and FPD 3 for every X-ray emission is L, although the X-ray tube 2 and FPD 3 move the moving distance L for each X-ray emission (X-ray irradiation), images in the shape of strips with width L in the central cut plane (plane parallel to the body axis y and parallel in a horizontal plane in FIG. 19) are geometrically enlarged and projected with a width Ls=L× enlargement factor on the detecting plane of FPD 3 (see Ls and L in FIG. 19). Subscript (suffix) M of $O_M$ in FIGS. 14-16 indicates the number of radiograms (i.e. the number of times of X-ray emission).

FIG. 17 shows a relationship with projection images of one section of the central cut plane. In FIG. 17, cut plane $T_8$ of N=8 (8th) is taken for example, to show that the images which project $T_8$ are decomposed images $O_{81}, O_{72}, O_{63}, \ldots$, and $O_{18}$. N in FIG. 17 is the integral part of the length of FPD 3 divided by image $O_{IJ}$ (i.e. length of FPD 3/image $O_{IJ}$), which shows how many $O_{IJ}$ can be acquired with one detecting plane. A relationship between the cut surface and projection image $O_{IJ}$ is shown in FIG. 18. The projection image group of $T_I$ is the following images indicated by the arrows in the figure. This may be depicted as in FIG. 19. FIG. 19 shows the Kth and (K+1)th cut planes $T_K$ and $T_{K+1}$.

When the X-ray tube 2 and FPD 3 move the moving distance L for every X-ray emission, portions in the shape of strips of width L on a patient plane (i.e. cut plane on the patient M) T as noted hereinbefore are given as projection images of width Ls as shown in FIG. 19. As described with reference to FIGS. 6-8 also, $O_{IJ}$ is the Jth strip image of the Ith projection image, i.e. the decomposed image at the time of projection angle $\theta_N$ (projection angle $\phi_N$ in FIGS. 9-19) obtained from the Ith pitch movement. Width L is pitch d noted hereinbefore (see FIG. 6).

Information around the patient plane $T_K$ is reconstructed by $O_{KI}, O_{(K-1)2}, O_{(K-2)3}, O_{(K-(N-1))N}$ as shown in FIG. 19(a). The Feldkamp method noted hereinbefore is applied to this reconstruction. And information around the following patient plane $T_{K+1}$ is reconstructed by $O_{(K+1)I}, O_{K2}, O_{(K-1)3}, \ldots O_{(K+1-(N-1))N}$ as shown in FIG. 19(b). The Feldkamp method is similarly applied to the reconstruction.

From strip portion $T_1$ at the extreme end (starting point) of the patient plane, each strip portion $T_I$ is separated by distance L×(I−1). Therefore, each image is shifted in y-direction by L×(I−1)×SID/SOD. In order to obtain reconstructed images (sectional images) of the entire patient M, reconstructed images of the peripheries of each strip portion $T_I$ may be obtained and processes may be carried out to join (compose) them. A reconstructed image fi(r) around $T_I$ is expressed by the following equation (7) applied from the foregoing equation (1).

[Numeric 2]

$$fi(r) = 1/4\pi^2 \int W_2 \int g_y O_{(I-(\phi-1))\phi} W_1 dY' d\phi \quad (7)$$

An entire reconstructed image joining (composing) fi(r) is expressed by the following equation (8).

[Numeric 3]

$$f(r) = \sum_{I=N}^{M} 1/4\pi^2 \int W_2 \int g_y O_{(I-(\phi-1))\phi} W_1 dY' d\phi \quad (8)$$

With this equation, it is possible to change the order of the back projection and the combination of images according to $\phi$. The change in the order of calculation results in the following equation (9).

[Numeric 4]

$$f(r) = 1/4\pi^2 \int W_2 \int g_y \sum_{I=N}^{M} O_{(I-(\phi-1))\phi} W_1 dY' d\phi \quad (9)$$

Here, $\Sigma O_{(I-(\phi-1))\phi}$ in the above equation (9) (where $\Sigma$ is a total of $O_{(I-(\phi-1))\phi}$ with suffix I=N, ..., to M) is a combination of images with projection angle $\phi$, i.e. an elongated image (long image) $P_\phi$. Therefore, f(f) is finally expressed as in the following equation (10).

[Numeric 5]

$$f(r) = 1/4\pi^2 \int W_2 \int g_y P_\phi W_1 dY' d\phi \quad (10)$$

In such long tomosynthesis, this can reconstruct each fragment (section) in the longitudinal direction (that is, the direction of the body axis which is the longitudinal direction of the patient M) by the Feldkamp method, and it can be said that a composition (combination) of the reconstruction results is equivalent to a reconstruction by the Feldkamp method using long images as the projection images. That is, the same effect is acquired even when reconstruction is carried out after obtaining long images.

According to the X-ray body section imaging apparatus in this embodiment, data of a long field of view of the body axis z which is the longitudinal direction can be obtained from the FPD 3 by constructing that the X-ray tube 2 and flat panel X-ray detector (FPD) 3 are movable parallel to each other in the same direction along the body axis z which is the longitudinal direction of the patient M. On the other hand, whenever the X-ray tube 2 and FPD 3 move every pitch (predetermined distance), X rays are intermittently emitted from the X-ray tube 2, and the FPD 3 detects X rays transmitted through the patient M intermittently irradiated. And the image decomposing unit 9b decomposes the X-ray images for every pitch noted above. The image composing unit 9c composes the decomposed images for each of the same projection angles to obtain projection images for each projection angle. Therefore, the reconstruction processing unit 9d can obtain a sectional image having a long field of view in the longitudinal direction by carrying out a reconstruction process based on the composed projection images.

In this embodiment, the X-ray tube 2 and FPD 3 move parallel to each other at the same speed. With the X-ray tube 2 and FPD 3 moving parallel to each other at the same speed, the projection angle can be maintained at the same angle. The X-ray tube 2 and FPD 3 can be moved for a long time. As a result, a sectional image with a longer field of view can be obtained.

When the patient M is human as in this embodiment, a 3D grasp and diagnosis of pathological changes over large ranges can be carried out, producing also an effect of contributing to improved diagnostic performance. It provides also an effect of enabling a 3D grasp of scoliosis and a 3D grasp of leg bolus chasing. Here, the leg bolus chasing is a technique of scanning a leg for every cut plane. By applying images in cut planes to the projection images noted hereinbefore (see FIGS. 7 and 8), leg bolus chasing can be carried out easily.

This embodiment provides the monitor 13 for displaying and outputting the sectional images obtained by the reconstruction processing unit 9d. With such monitor 13, it is possible to browse displays. Instead of being limited to the display device like the monitor 13, a printing device represented by a printer may be provided. In this case, the printing device corresponds to the output device in this invention. With the printing device outputting prints, it is possible to browse the prints. Both the monitor 13 and a printer may be provided.

This invention is not limited to the foregoing embodiment, but may be modified as follows:

(1) In the foregoing embodiment, the X-ray body section imaging apparatus has been described as an example of radiographic apparatus. The invention may be applied to a radiographic apparatus, such as an ECT (Emission Computed Tomography) apparatus represented by a PET (Positron Emission Tomography) apparatus or a SPECT (Single Photon Emission CT) apparatus, which carries out radiation image pickup by detecting radiation other than X rays (gamma rays in the case of the PET apparatus) and obtaining radiographic images based on the detected radiation.

(2) In the foregoing embodiment, the flat panel X-ray detector has been described as an example of radiation detecting device. There is no limitation as long as the device is an X-ray detecting device used generally, such as an image intensifier (I.I.). As in the case of being applied to an ECT apparatus, as in modification (1) above, there is no limitation as long as it is a radiation detecting device used generally.

(3) The foregoing embodiment provides the output device represented by the monitor 13. The output device is not absolutely necessary.

(4) In the foregoing embodiment, the radiation emitting device represented by the X-ray tube 2 and the radiation detecting device represented by the FPD 3 are moved parallel to each other at the same speed. As long as the radiation emitting device and radiation detecting device are moved parallel relative to each other in the same direction along the longitudinal direction of the patient, one of them may be moved fast and the other moved slowly.

(5) In the foregoing embodiment, only the radiation emitting device represented by the X-ray tube 2 and the radiation detecting device represented by the FPD 3 are moved, and the top board 1 supporting the patient M is fixed, whereby the radiation emitting device and radiation detecting device are moved parallel relative to each other in the same direction along the longitudinal direction of the patient. The invention is not limited to a specific movement as long as the radiation emitting device and radiation detecting device are moved parallel relative to each other in the same direction along the longitudinal direction of the patient. For example, the radiation emitting device represented by the X-ray tube 2 and the radiation detecting device represented by the FPD 3 may be fixed, and only the top board 1 supporting the patient M may be moved, whereby the radiation emitting device and radiation detecting device are moved parallel relative to each other in the same direction along the longitudinal direction of the patient. The radiation emitting device represented by the X-ray tube 2 and the radiation detecting device represented by the FPD 3 may be moved, and the top board 1 supporting the patient M may also be moved in the longitudinal direction, whereby the radiation emitting device and radiation detecting device are moved parallel relative to each other in the same direction along the longitudinal direction of the patient.

The invention claimed is:

1. A radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device and the radiation detecting device being constructed movable parallel relative to each other in the same direction along a longitudinal direction of the patient, the radiation emitting device intermittently emitting radiation and the radiation detecting device detecting radiation transmitted through the patient irradiated intermittently whenever the radiation emitting device and the radiation detecting device move every predetermined distance relative to the patient, said apparatus comprising an image decomposing device for decomposing the radiographic image for the every predetermined distance, an image composing device for composing the decomposed images for each of the same projection angles to obtain a projection image for each projection angle, and a reconstruction processing device for carrying out a reconstruction process based on the composed projection images to obtain a sectional image.

2. The radiographic apparatus according to claim 1, wherein the radiation emitting device and the radiation detecting device are movable parallel relative to each other at an equal speed relative to the patient.

3. The radiographic apparatus according to claim 2, further comprising an output device for outputting the sectional image obtained by the reconstruction processing device.

4. The radiographic apparatus according to claim 1, further comprising an output device for outputting the sectional image obtained by the reconstruction processing device.

* * * * *